United States Patent
Yokoi et al.

(10) Patent No.: US 7,083,579 B2
(45) Date of Patent: Aug. 1, 2006

(54) ENCAPSULATED MEDICAL DEVICE AND METHOD OF EXAMINING, CURING, AND TREATING INTERNAL REGION OF BODY CAVITY USING ENCAPSULATED MEDICAL DEVICE

(75) Inventors: Takeshi Yokoi, Hino (JP); Hironobu Takizawa, Hachioji (JP); Hidetake Segawa, Hachioji (JP); Hideyuki Adachi, Sagamihara (JP)

(73) Assignee: Olympus Corporation, Toyko (JP)

( * ) Notice: Subject to any disclaimer, the term of this patent is extended or adjusted under 35 U.S.C. 154(b) by 632 days.

(21) Appl. No.: 10/251,443

(22) Filed: Sep. 20, 2002

(65) Prior Publication Data

US 2003/0060734 A1    Mar. 27, 2003

(30) Foreign Application Priority Data

Sep. 27, 2001    (JP)    ............................. 2001-297703

(51) Int. Cl.
*A61B 5/117*    (2006.01)
*A61B 5/103*    (2006.01)
(52) U.S. Cl. ..................................... 600/593
(58) Field of Classification Search ............... 600/549, 600/561, 593, 309, 437, 562; 604/28, 65; 607/92; 606/32; 128/903
See application file for complete search history.

(56) References Cited

U.S. PATENT DOCUMENTS 4,028,687 A    6/1977    Hamaguchi et al.

FOREIGN PATENT DOCUMENTS

| JP | 7-111985 | 5/1995 |
| JP | 9-327447 | 12/1997 |
| JP | 2000-342522 | 12/2000 |

*Primary Examiner*—Max F. Hindenburg
*Assistant Examiner*—Brian Szmal
(74) *Attorney, Agent, or Firm*—Scully, Scott, Murphy & Presser, P.C.

(57) ABSTRACT

An encapsulated medical device includes a radio antenna through which the encapsulated medical device transmits or receives a radio wave to or from an extracorporeal device. The encapsulated medical device is passed through the lumen of a body cavity in order to examine, cure, or treat an internal region of the body cavity under the control of the extracorporeal device. A capsule body included in the encapsulated medical device has an extended portion formed at an upper end of one axis of a cross section of the capsule body cut at right angle to the longitudinal axis thereof. The capsule body has a linkage hole bored in the extended portion thereof to allow a fluid such as a gas or humor to flow into forward and backward parts of the lumen through the hole.

31 Claims, 19 Drawing Sheets

FIG.1
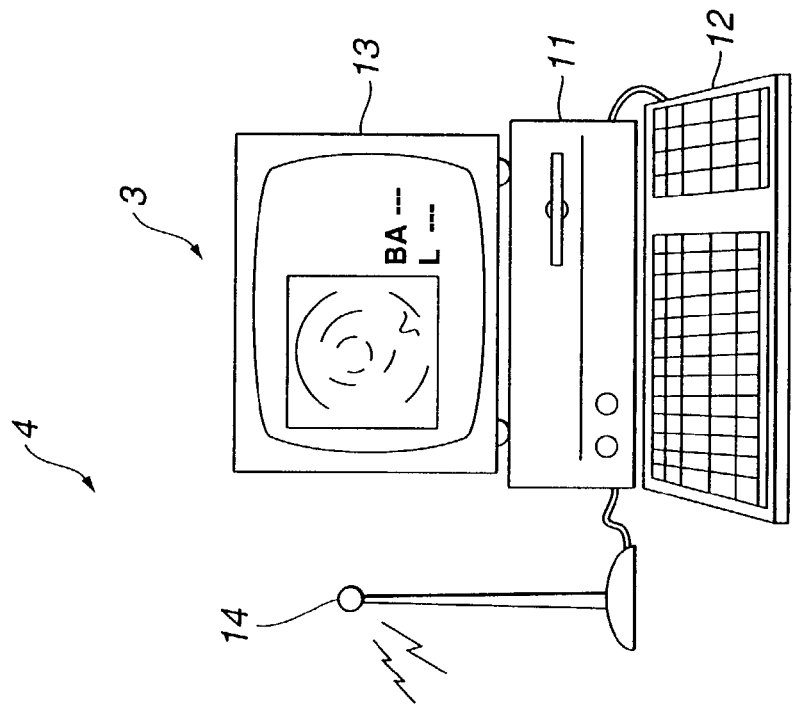
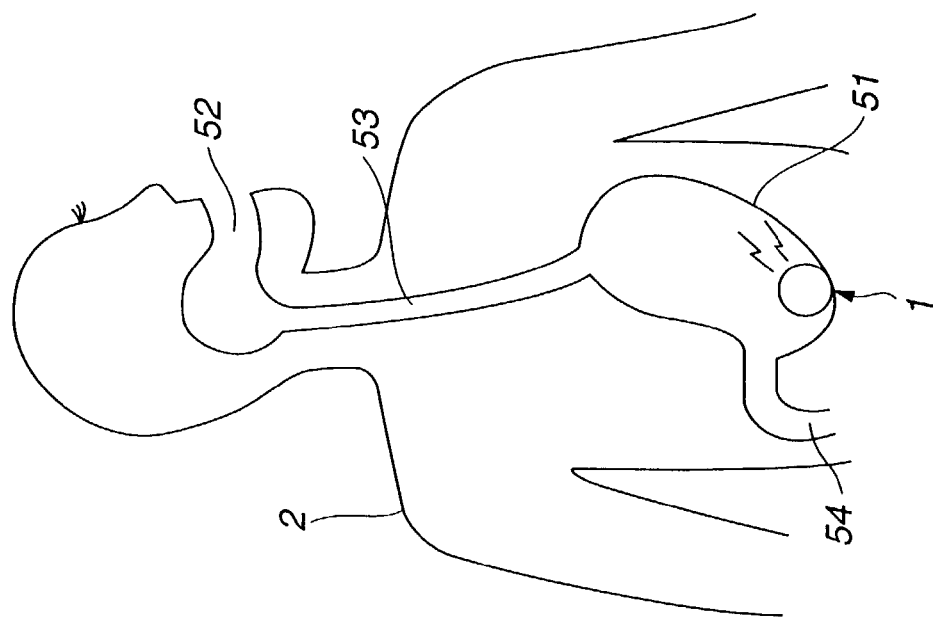

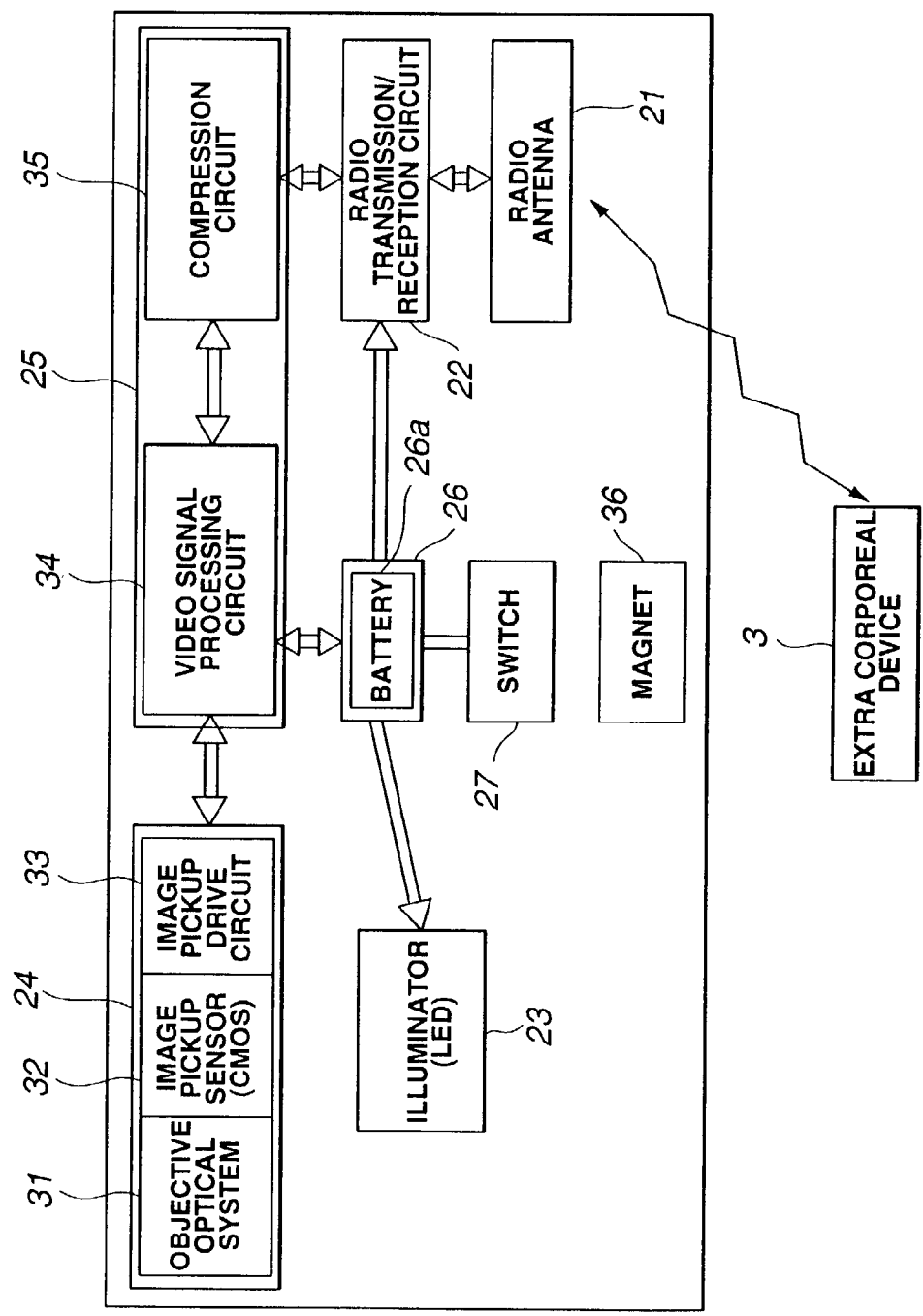

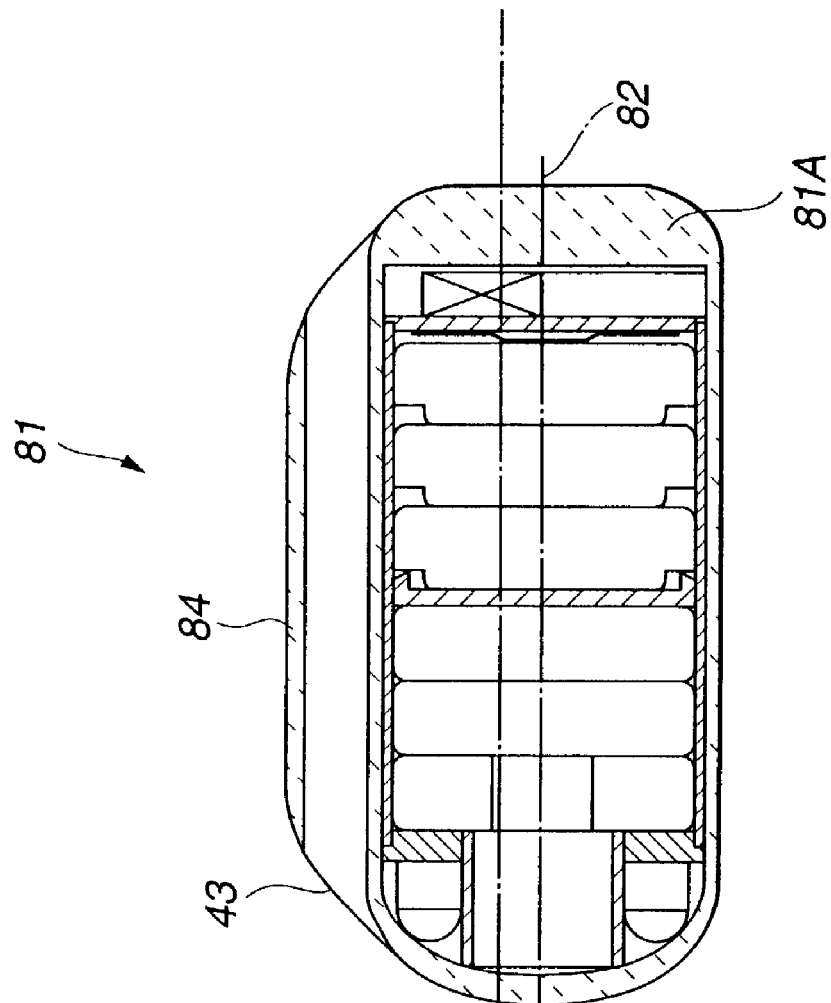
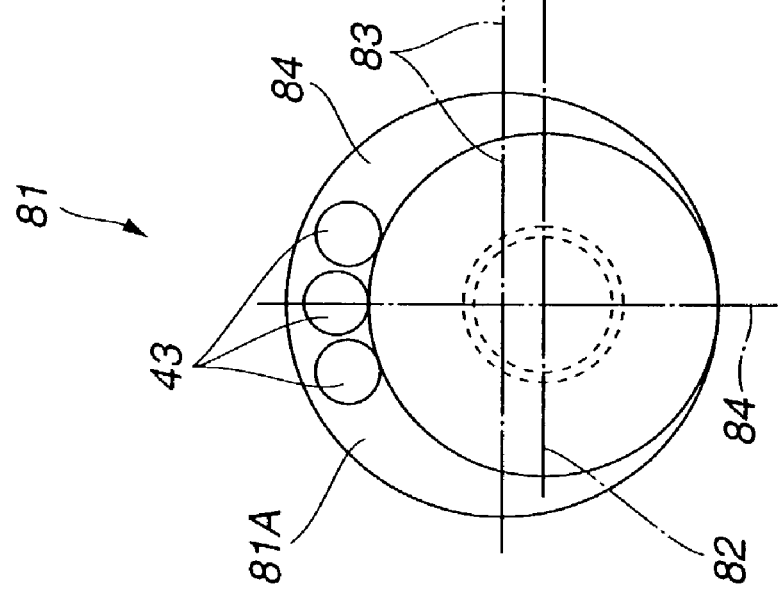

FIG.10B FIG.10A
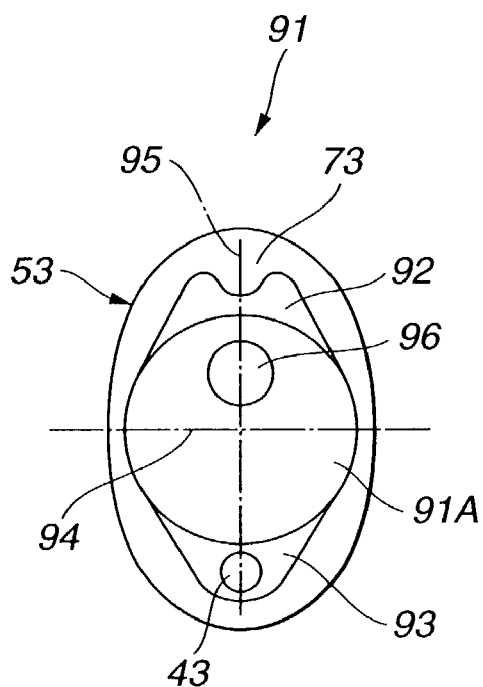
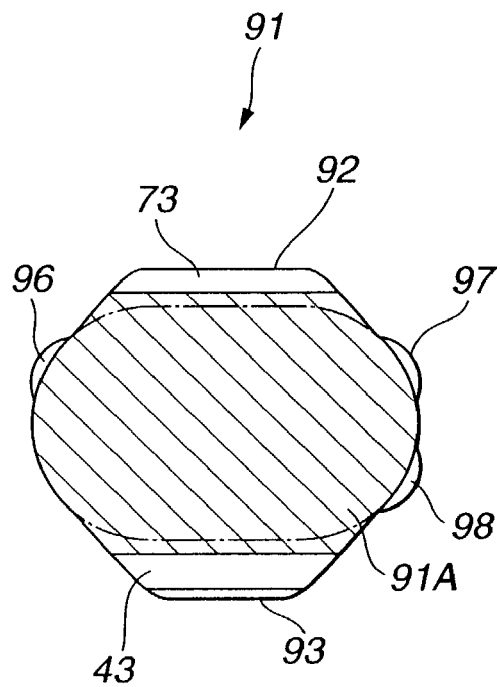
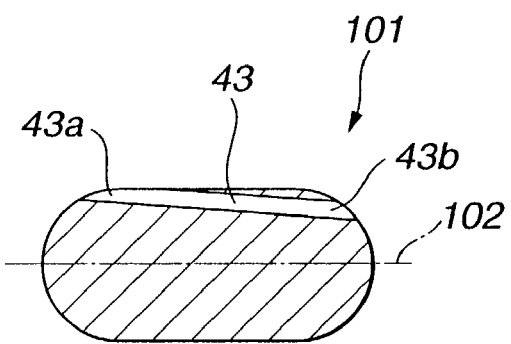
FIG.11A
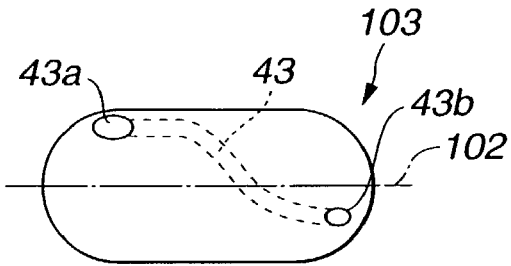
FIG.11B

PLANE FOR
ULTRASONIC
TOMOGRAPHY
(360°C)

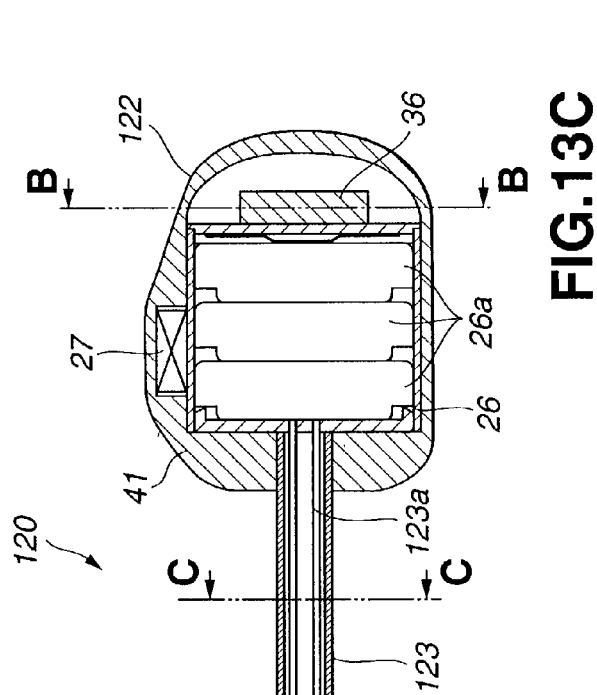
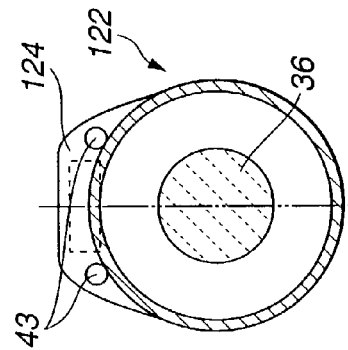
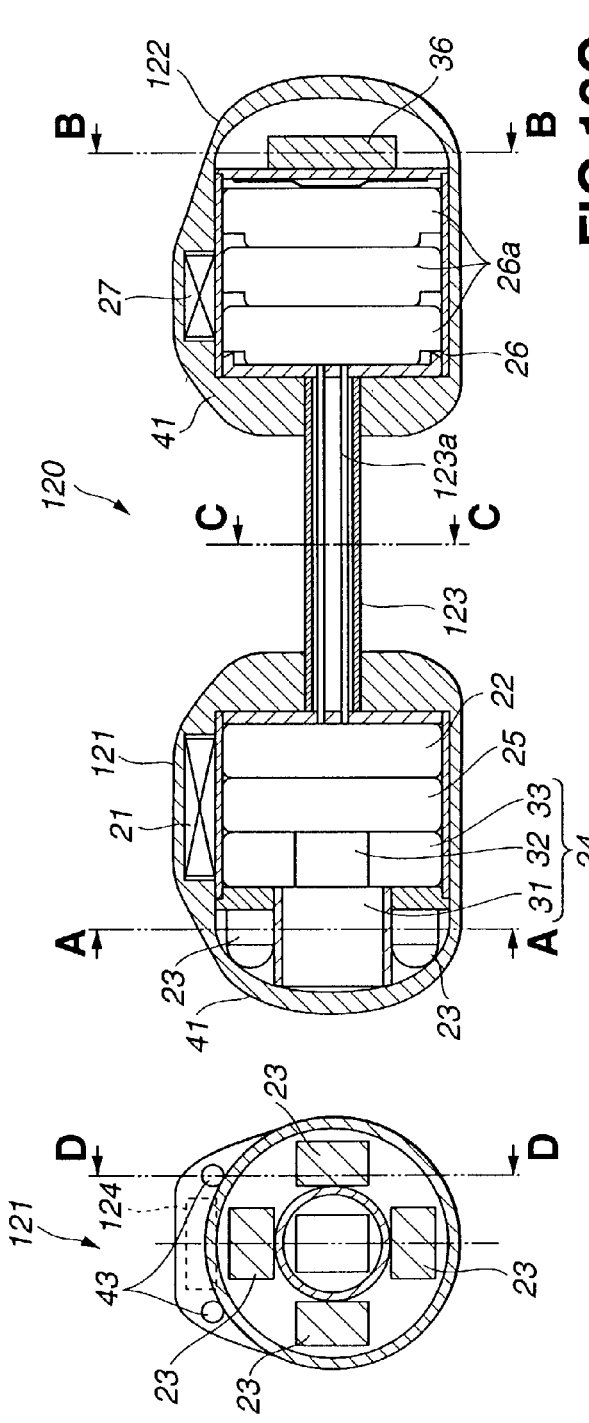
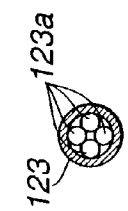

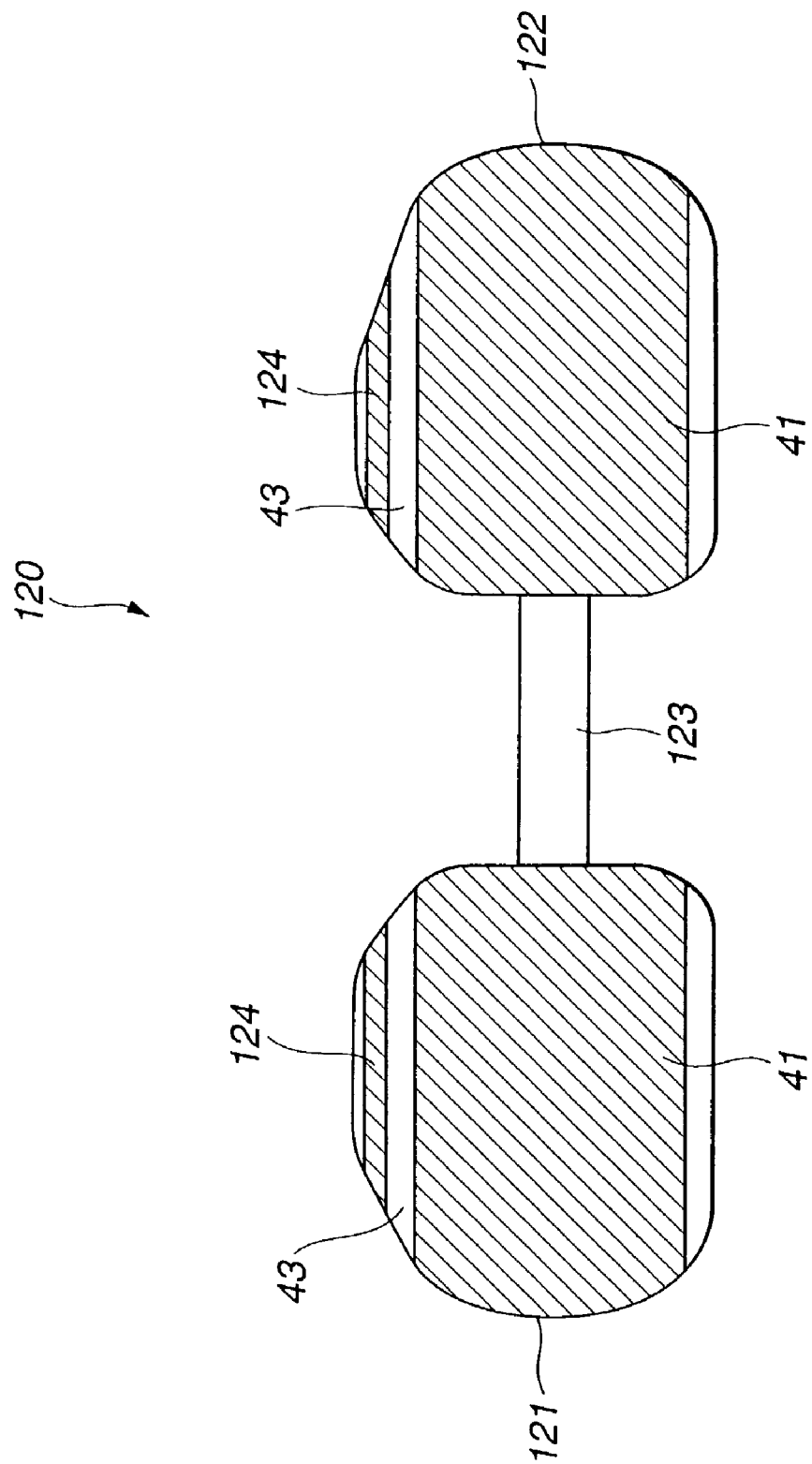

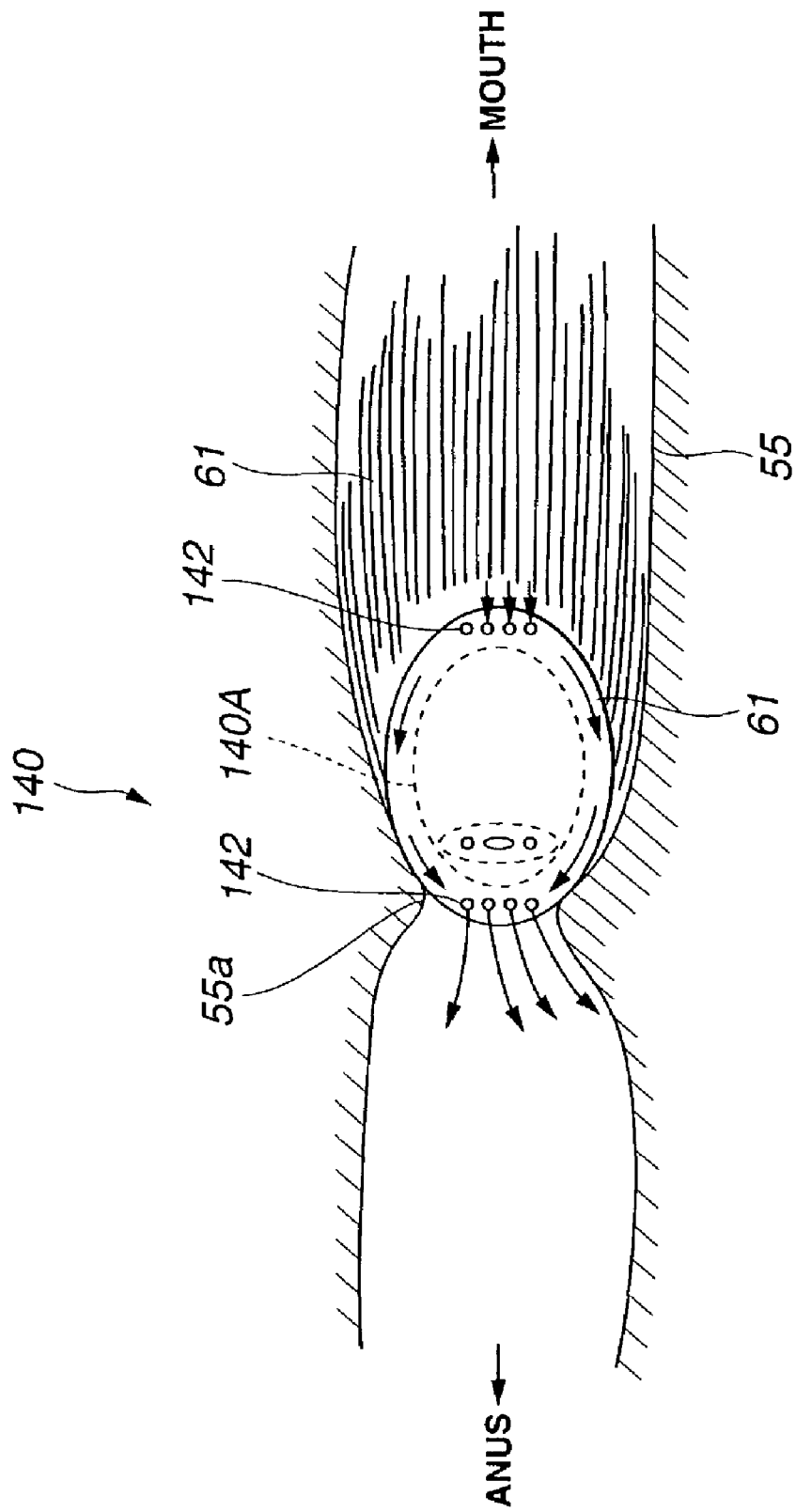

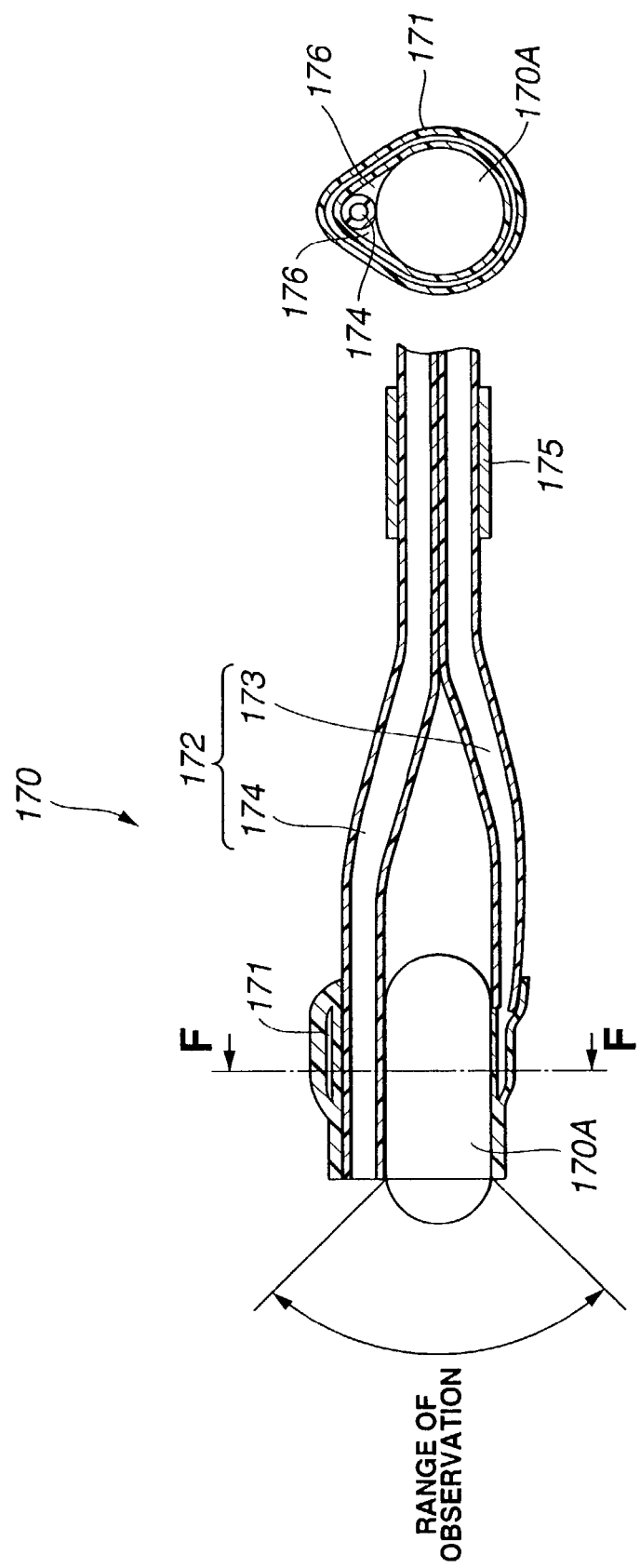

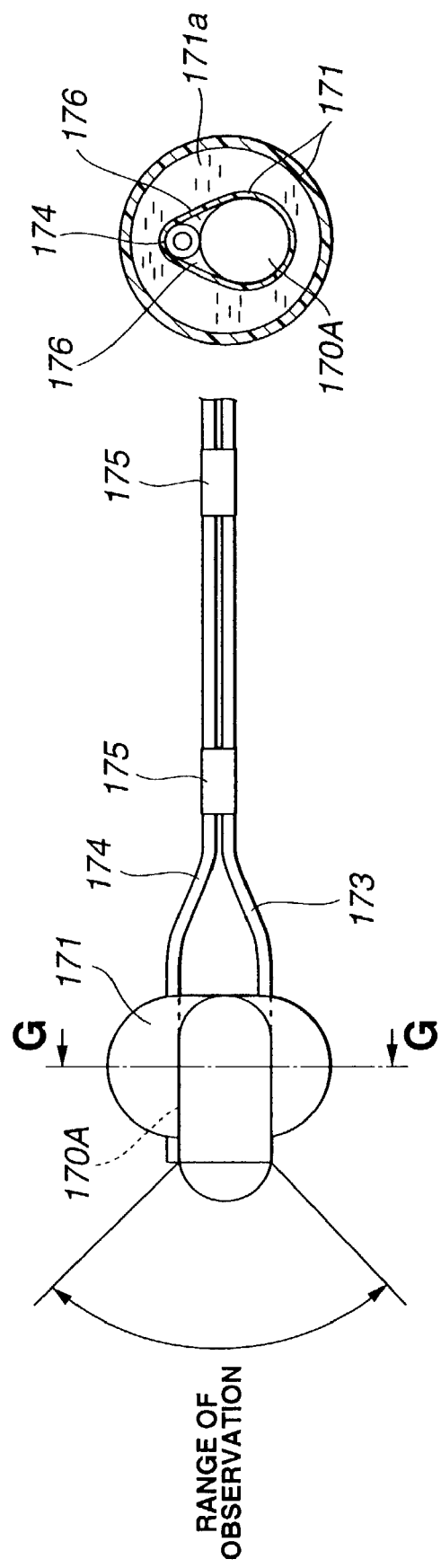

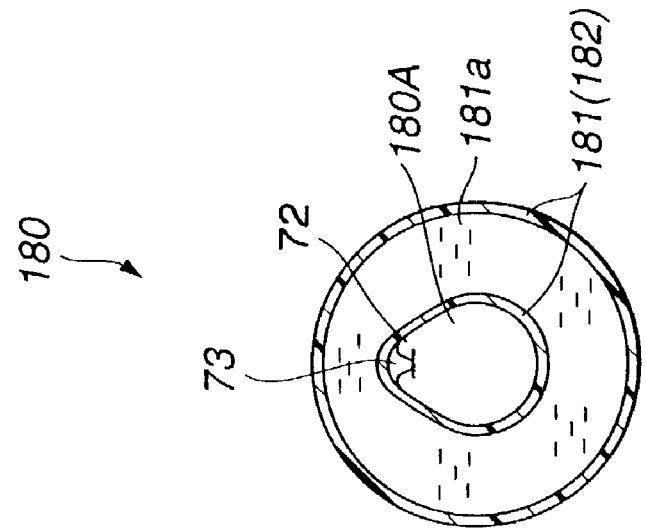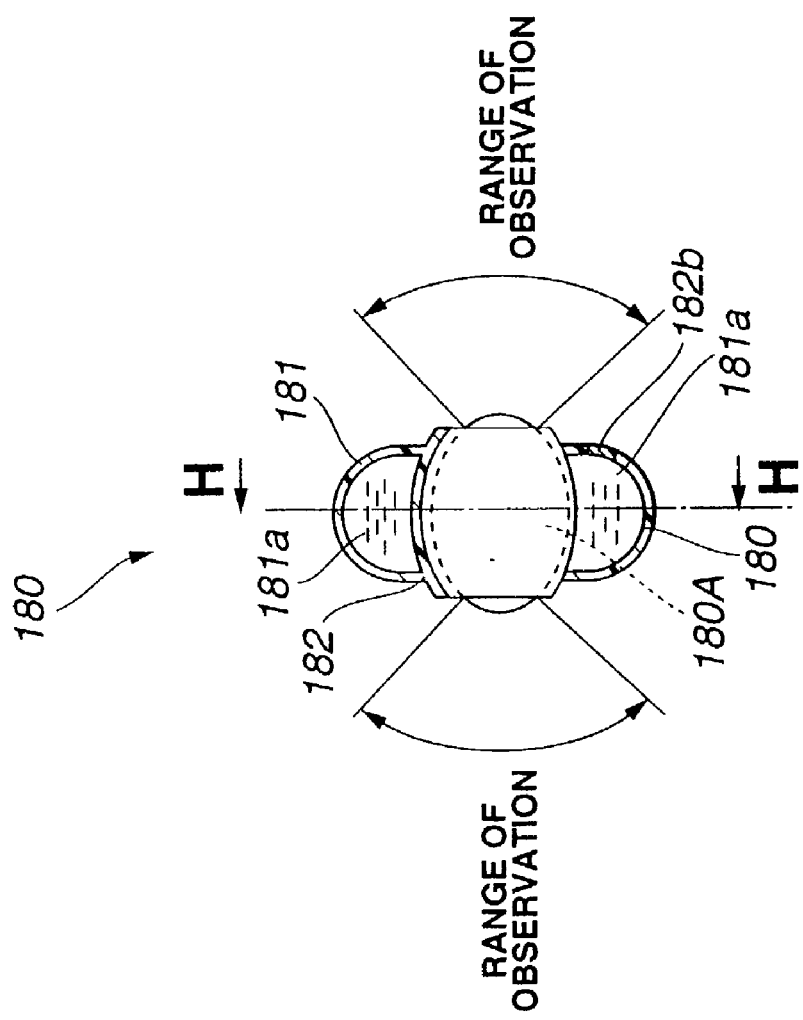

ENCAPSULATED MEDICAL DEVICE AND METHOD OF EXAMINING, CURING, AND TREATING INTERNAL REGION OF BODY CAVITY USING ENCAPSULATED MEDICAL DEVICE

This application claims the benefit of Japanese Application No. 2001-297703 filed in Japan on Sep. 27, 2001, the contents of which are incorporated by reference.

BACKGROUND OF THE INVENTION

1. Field of the Invention

The present invention relates to an encapsulated medical device, and a method of examining, curing, and treating an internal region of a body cavity using the encapsulated medical device.

2. Description of the Related Art

Conventionally, an endoscope is used to examine, cure, or treat an intended region by inserting an elongated inserting section thereof, which is coupled to an operation unit, into a body cavity. It is however hard to keep the endoscope inserted therein for a prolonged period of time.

For example, Japanese Unexamined Patent Application Publication No. 2000-342522, and Japanese Unexamined Patent Application Publications Nos. 7-111985 and 9-327447 which the present applicant filed previously have proposed peroral medical devices capable of examining, curing, or treating an internal region.

The Japanese Unexamined Patent Application Publication No. 2000-342522 has proposed a peroral endoscope. The peroral endoscope has a balloon, which is used to immobilize the endoscope at an intended region of the lumen of a body cavity, included in the front part of an inserting section thereof.

The Japanese Unexamined Patent Application Publication Nos. 7-111985 and 9-327447 propose encapsulated medical devices. The encapsulated medical devices have various sensor means and power supply means disposed on the surface of a capsule body.

However, in the peroral endoscope described in the Japanese Unexamined Patent Application Publication No. 2000-342522 has a drawback that the balloon comes into close contact with the internal surface of a body cavity to block the lumen of the body cavity. Consequently, the balloon comes to a standstill on the internal surface of the body cavity in a stenosed part thereof. Moreover, in the peroral endoscope, a hole or a groove, which allows a fluid such as a gas or humor to flow forwards or backwards in the lumen, is not formed between the balloon and an endoscope body, in the balloon itself, nor in a portion of the endoscope body other than the portion having the balloon. Therefore, when the peroral endoscope described in the Japanese Unexamined Patent Application Publication No. 2000-342522 comes to a standstill on the internal surface of the body cavity in the stenosed part thereof, a fluid such as a gas or humor cannot flow forwards or backwards in the lumen.

In contrast, the encapsulated medical devices described in the Japanese Unexamined Patent Application Publication Nos. 7-111985 and 9-327447 have a plurality of means including various sensor means and power supply means fixed on the periphery of a capsule body. The outer diameter of the capsule body is large when all over the periphery thereof is included. The capsule body therefore comes into close contact with the internal surface of a body cavity to block the lumen of the body cavity. Consequently, the capsule body comes to a standstill on the internal surface of the body cavity in a stenosed part thereof.

In the encapsulated medical devices, concave parts of the periphery of the capsule body created by various sensor means and the power supply means are shallow. Therefore, when the capsule body comes to a standstill on the internal surface of the body cavity in a stenosed part thereof, the concave parts hardly allow a fluid such as a gas or humor to flow forwards or backwards in the lumen. The encapsulated medical devices have been developed without concern about the incident that the capsule body may come to a standstill in a stenosed part of a lumen. No description has been made of the incident that the capsule body may come to a standstill in a stenosed part of a lumen.

For example, in relation to the encapsulated medical device, alarm devices for livestock or especially for delivery including the one described in U.S. Pat. No. 4,028,687 have been proposed. The alarm device is inserted into the birth canal so that it will alarm at the time of delivery.

SUMMARY OF THE INVENTION

Accordingly, an object of the present invention is to provide an encapsulated medical device and a method of examining, curing, or treating an internal region of a body cavity using the encapsulated medical device. Herein, the encapsulated medical device allows a fluid such as a gas or humor to flow forwards or backwards in the lumen even when a capsule body comes to a standstill in a stenosed part of the body cavity. Nevertheless, the capsule body is highly general-purpose and the ease of swallowing of the encapsulated medical device does not deteriorate.

Another object of the present invention is to provide an encapsulated medical device capable of safely protecting the internal surface of a body cavity despite its coming into close contact with the internal surface thereof, and a method of examining, curing, or treating an internal region of a body cavity using the encapsulated medical device.

Still another object of the present invention is to provide an encapsulated medical device permitting a doctor or a co-medical to judge whether a disease, bleeding, or any other abnormality is found or to judge at what position or in what state a capsule is passing, and a method of examining, curing, or treating an internal region of a body cavity using the encapsulated medical device.

Still another object of the present invention is to provide an encapsulated medical device that when coming into close contact with the internal surface of, for example, the small intestine in a stenosed part thereof to block the lumen of the small intestine, allowing a fluid such as a gas or humor to flow into regions spreading ahead of and behind the stenosed part, and a method of examining, curing, or treating an internal region of a body cavity using the encapsulated medical device.

Still another object of the present invention is to provide an encapsulated medical device permitting diagnosis of whether an abnormality is found in the direction of the depth of a deep region in the lumen of, for example, the small intestine, and a method of examining, curing, or treating an internal region of a body cavity using the encapsulated medical device.

According to the present invention, an encapsulated medical device consists mainly of a capsule body and fluid passage forming means. The capsule body passes through the lumen of a body cavity so as to examine, cure, or treat an internal region of the body cavity. The fluid passage forming means is included in the capsule body. When the capsule body passes through the lumen of a body cavity, if the capsule body comes into close contact with the internal surface of the body cavity to block the lumen of the body cavity, the fluid passage forming means forms a fluid passage which links the forward and backward parts of the lumen.

According to the method of examining, curing; or treating an internal region of a body cavity using an encapsulated medical device in accordance with the present invention, fluid passage forming means included in a capsule body, when the capsule body comes into close contact with the internal surface of a body cavity to block the lumen of the body cavity, forms a fluid passage that links the forward and backward parts of the lumen.

Other features of the present invention and the advantages thereof will be fully apparent from the description below.

BRIEF DESCRIPTION OF THE DRAWINGS

FIG. 1 shows the overall configuration of a medical system including a first embodiment of the present invention;

FIG. 2 is a circuit block diagram showing an encapsulated medical device in accordance with the first embodiment of the present invention;

FIG. 9A is a sectional view showing the components of an encapsulated medical device of a variant whose center axis passing through the center of the minor axis of a cross section thereof cut at right angle to the longitudinal axis thereof is deviated from the optical axis of an observation unit included therein;

FIG. 9B shows the appearance of the front part of the encapsulated medical device shown in FIG. 9A;

FIG. 10A shows the appearance of an encapsulated medical device of a variant that has extended portions of a capsule body formed on both ends of one axis of the cross section of the capsule body;

FIG. 10B shows the appearance of the front part of the encapsulated medical device that is shown in FIG. 10A and that is passing through the esophagus;

FIG. 11A is an explanatory diagram showing an encapsulated medical device of a variant that has a linkage hole bored obliquely with respect to the longitudinal axis thereof;

FIG. 11B is an explanatory diagram showing an encapsulated medical device of a variant that has a linkage hole bored to be tortuous with respect to the longitudinal axis thereof;

FIG. 13A is a sectional view showing the components of an encapsulated medical device in accordance with a second embodiment of the present invention;

FIG. 13B is an A—A sectional view of the encapsulated medical device shown in FIG. 13A;

FIG. 13C is a B—B sectional view of the encapsulated medical device shown in FIG. 13A;

FIG. 13D is a C—C sectional view of the encapsulated medical device shown in FIG. 13A;

FIG. 14 is a D—D sectional view of the encapsulated medical device shown in FIG. 13B;

FIG. 18 is an explanatory diagram showing a scene where the encapsulated medical device shown in FIG. 17 has come to a standstill in a stenosed part of the small intestine;

FIG. 22A is a sectional view showing an encapsulated medical device in accordance with a fourth embodiment of the present invention;

FIG. 22B is an F—F sectional view of the encapsulated medical device shown in FIG. 22A;

FIG. 23A shows the appearance of the encapsulated medical device that is shown in FIG. 22A and FIG. 22B and that has a balloon thereof expanded;

FIG. 23B is a G—G sectional view of the encapsulated medical device shown in FIG. 23A;

FIG. 24A is a sectional view showing an encapsulated medical device of a variant that has an armor member, which includes a balloon, freely detachably attached to the periphery of a capsule body; and FIG. 24B is an H—H sectional view of the encapsulated medical device shown in FIG. 24A.

DESCRIPTION OF THE PREFERRED EMBODIMENTS

Embodiments of the present invention will be described with reference to the drawings below.

First Embodiment

Figure 3C:
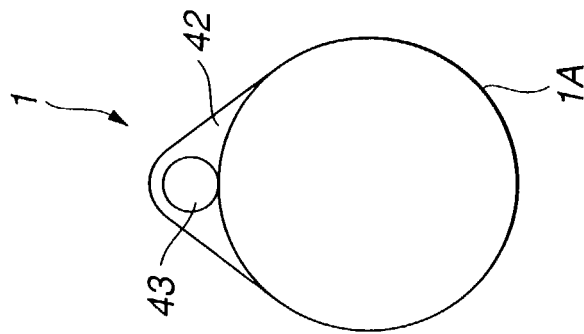
FIG. 3C shows the appearance of the back part of the encapsulated medical device shown in FIG. 3A.
Figure 3A:
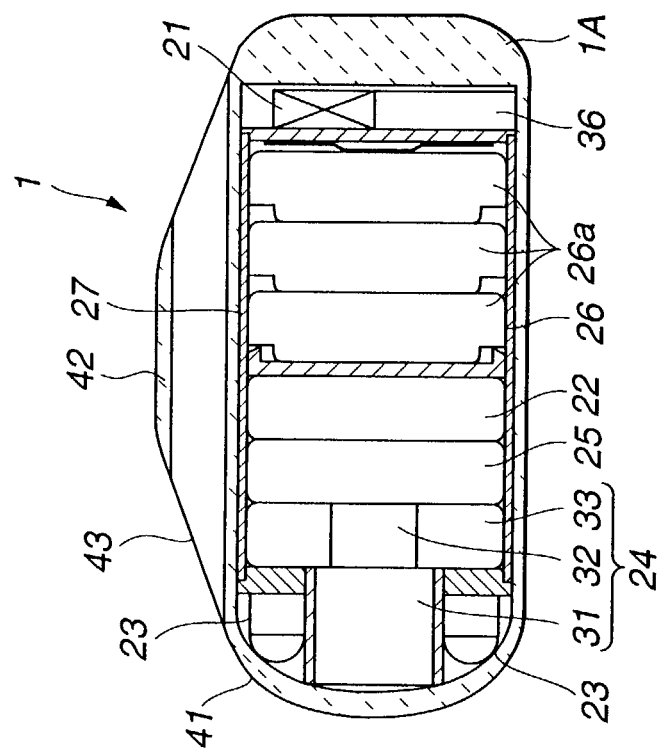
FIG. 3A is a sectional view showing the components of the encapsulated medical device shown in FIG. 2.
Figure 3B:
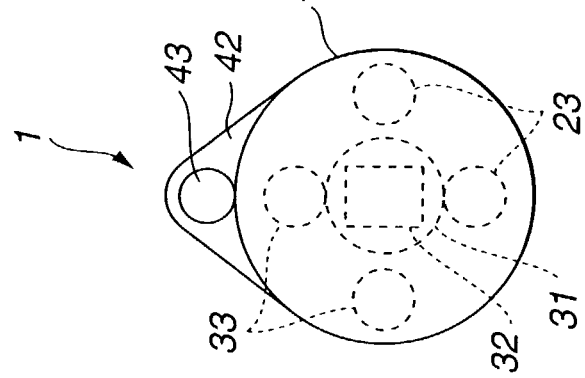
FIG. 3B shows the appearance of the front part of the encapsulated medical device shown in FIG. 3A.
Figure 4:
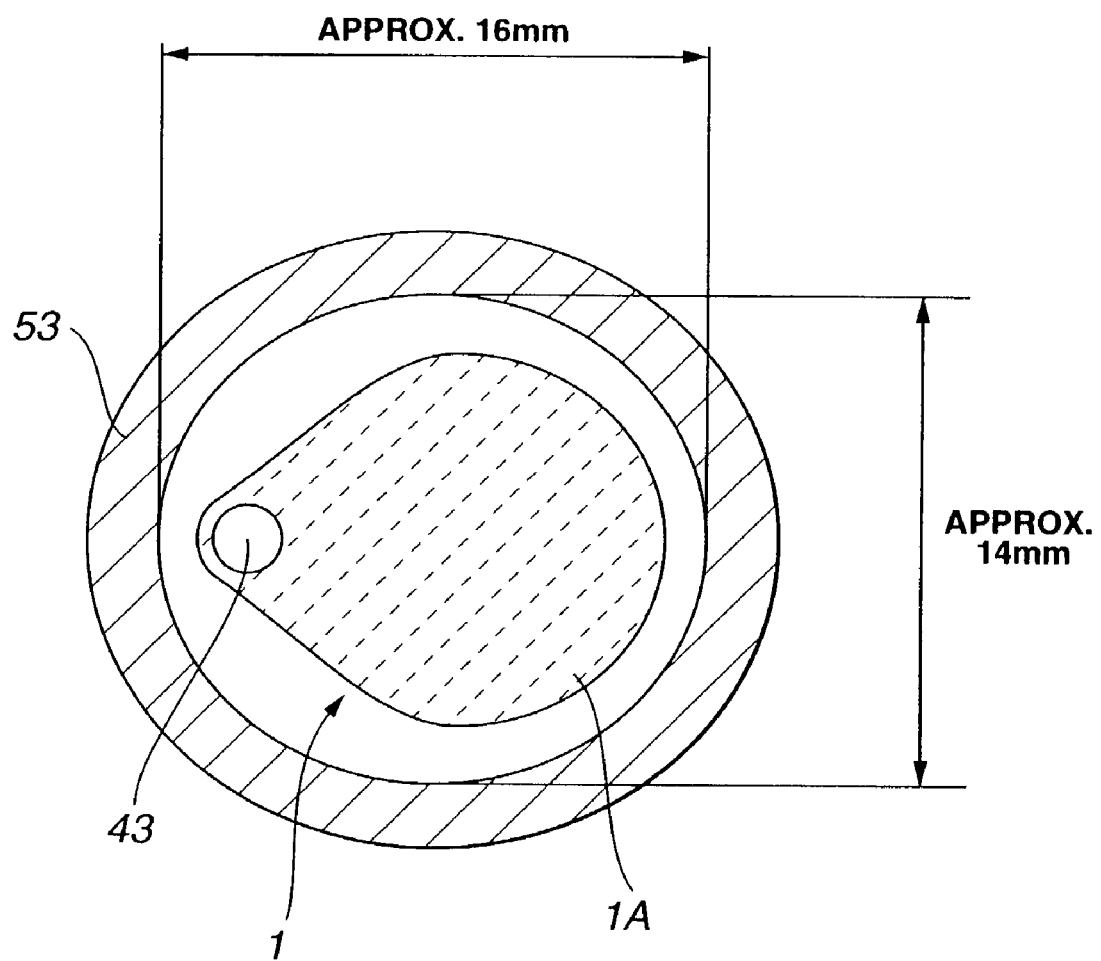
FIG. 4 is a sectional view showing a scene where the encapsulated medical device shown in FIG. 3A to FIG. 3C is passing through the esophagus.
Figure 5:
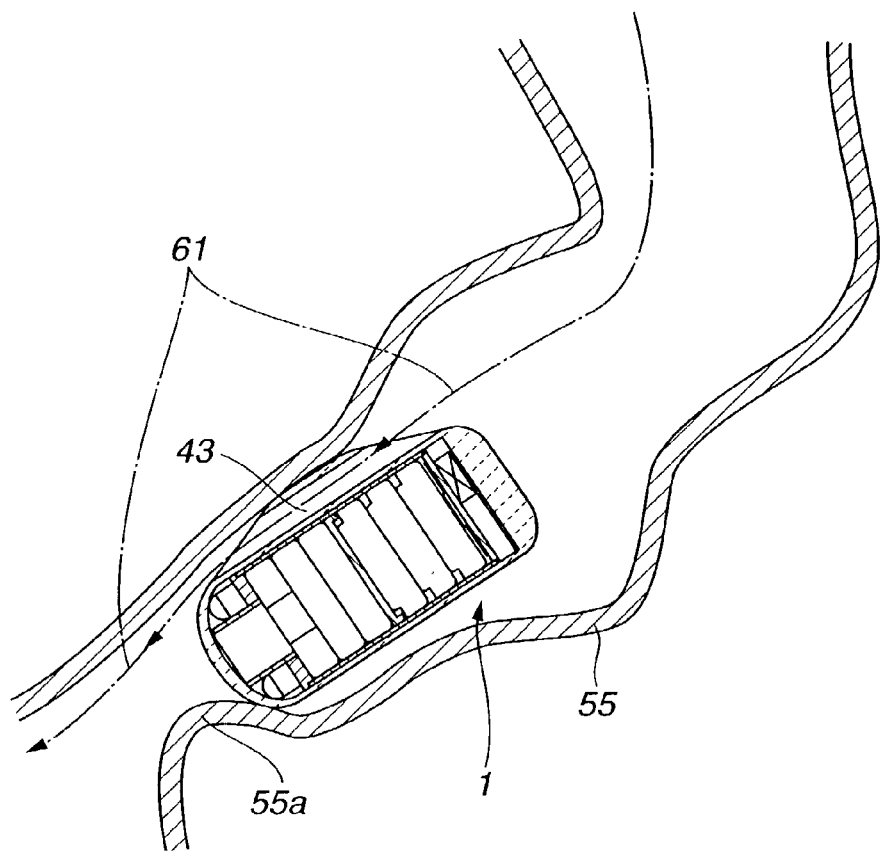
FIG. 5 is a sectional view showing a scene where the encapsulated medical device shown in FIG. 3A to FIG. 3C has come to a standstill in a stenosed part of the small intestine.
Figure 6:
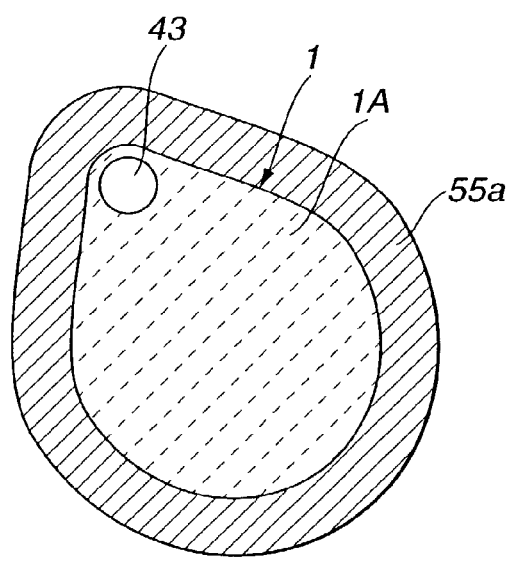
FIG. 6 is a sectional view of the encapsulated medical device shown in FIG. 5.
Figure 7:
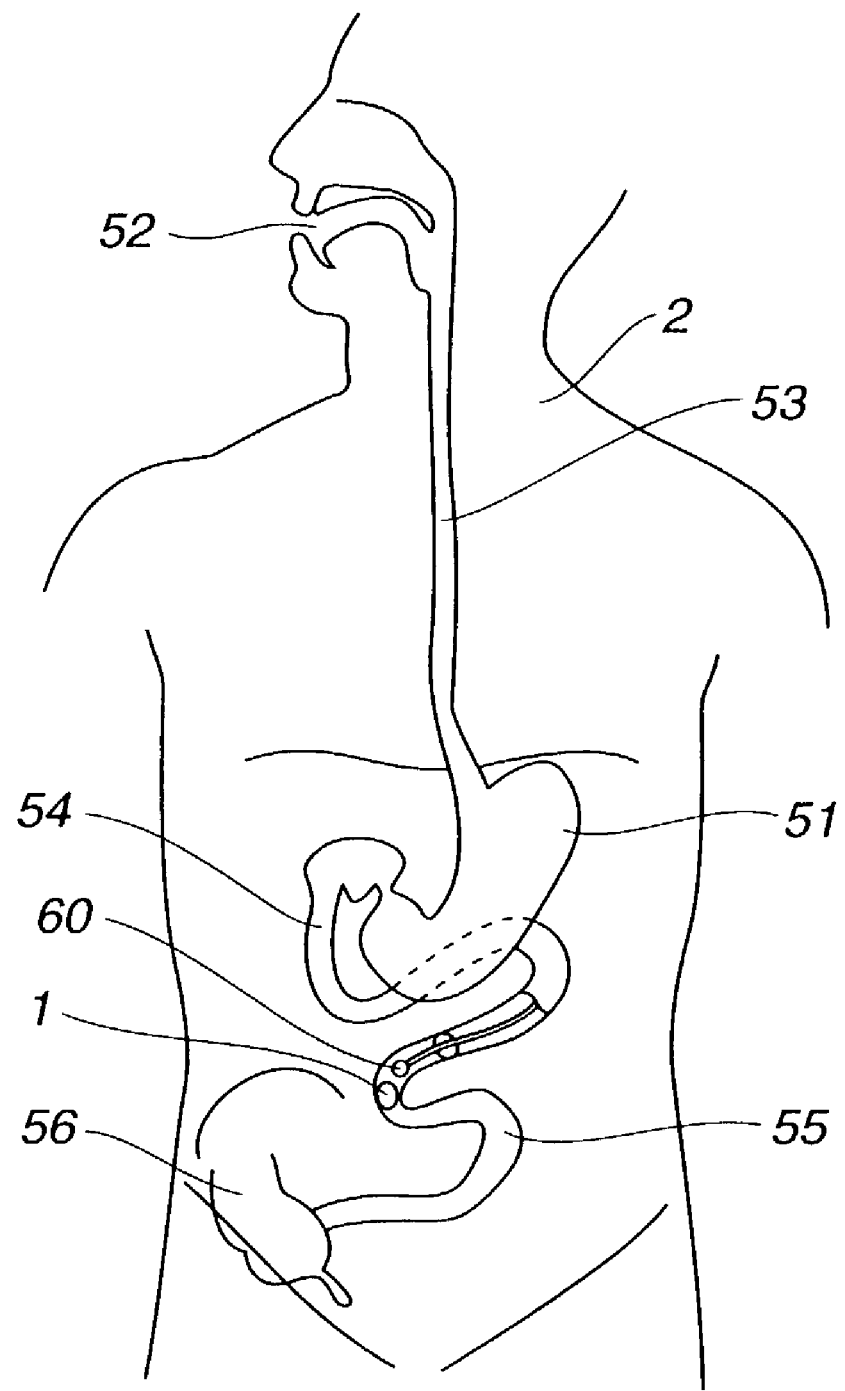
FIG. 7 is a schematic explanatory diagram showing a scene where the encapsulated medical device is being recovered using a string-like recovering tool.
Figure 8B:
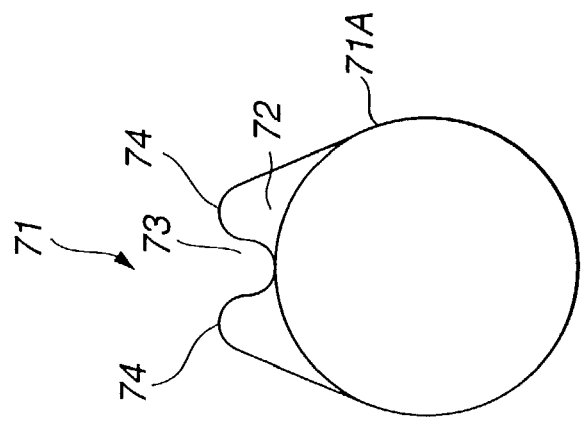
FIG. 8B shows the appearance of the front part of the encapsulated medical device shown in FIG. 8A.
Figure 8A:
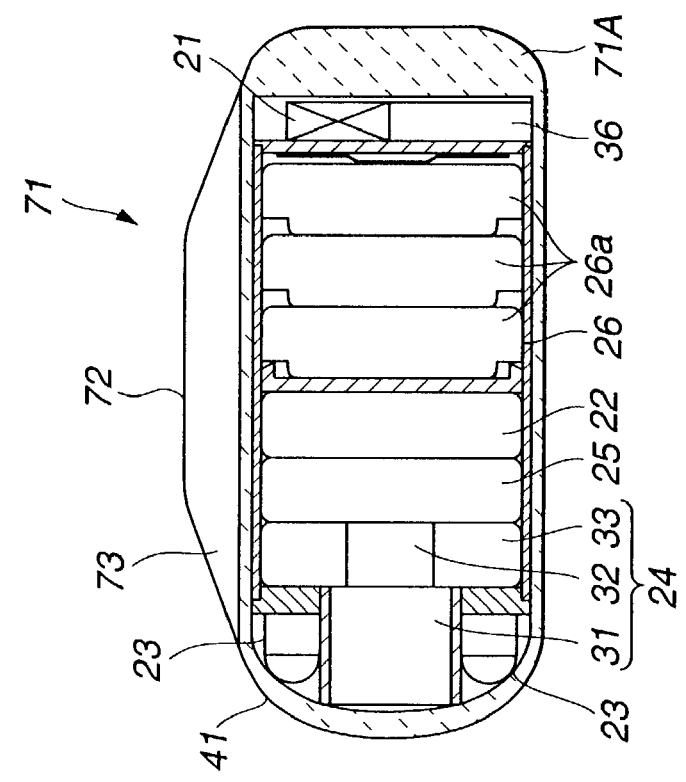
FIG. 8A is a sectional view showing the components of an encapsulated medical device of a variant having a linkage groove formed in an extended portion thereof.
Figure 8C:
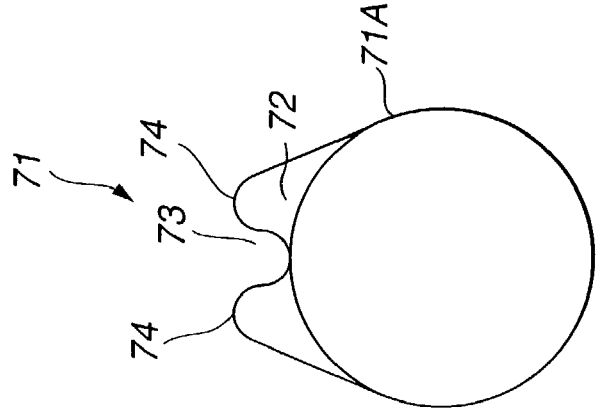
FIG. 8C shows the appearance of the back part of the encapsulated medical device shown in FIG. 8A.
Figure 12A:
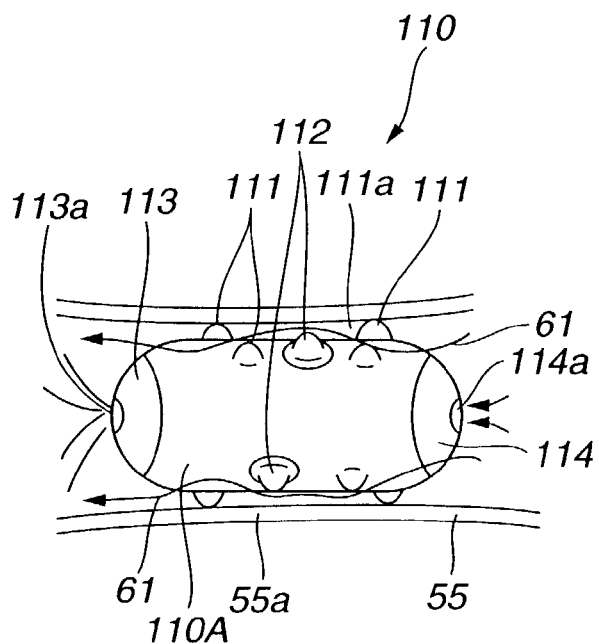
FIG. 12A is an explanatory diagram showing the appearance of an encapsulated medical device of a variant that has a plurality of projections formed on the periphery of a capsule body.
Figure 12B:
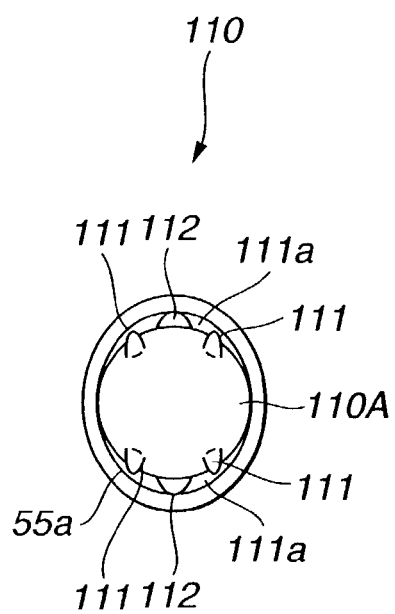
FIG. 12B shows the appearance of the front part of the encapsulated medical device shown in FIG. 12A.

FIG. 1 to FIG. 12B are concerned with a first embodiment of the present invention. FIG. 1 shows the overall configuration of a medical system including the first embodiment of the present invention. FIG. 2 is a circuit block diagram showing the encapsulated medical device in accordance with the first embodiment of the present invention. FIG. 3A is a sectional view showing the components of the encapsulated medical device shown in FIG. 2. FIG. 3B shows the appearance of the front part of the encapsulated medical device shown in FIG. 3A. FIG. 3C shows the appearance of the-back part of the encapsulated medical device shown in FIG. 3A. FIG. 4 is a sectional view showing a scene where the encapsulated medical device shown in FIG. 3A to FIG. 3C is passing through the esophagus. FIG. 5 is a sectional view showing a scene where the encapsulated medical device shown in FIG. 3A to FIG. 3C has come to a standstill in a stenosed part of the small intestine. FIG. 6 is a sectional view of the encapsulated medical device shown in FIG. 5. FIG. 7 is a schematic explanatory diagram showing a scene where the encapsulated medical device is being recovered using a string-like recovering tool. FIG. 8A is a sectional view showing the components of an encapsulated medical device of a variant that has a linkage groove formed in an extended portion thereof. FIG. 8B shows the appearance of the front part of the encapsulated medical device shown in FIG. 8A. FIG. 8C shows the appearance of the back part of the encapsulated medical device shown in FIG. 8A. FIG. 9A is a sectional view showing the components of an encapsulated medical device of a variant whose center axis passing through the center of the minor axis of a cross section thereof that is cut at right angle to the longitudinal axis thereof is deviated from the optical axis of an observation unit included therein. FIG. 9B shows the appearance of the front part of the encapsulated medical device shown in FIG. 9A. FIG. 10A shows the appearance of an encapsulated medical device of a variant that has extended portions of a capsule body formed on both ends of an axis of the cross section of the capsule body. FIG. 10B shows the appearance of the front part of the encapsulated medical device that is shown in FIG. 10A and that is passing through the esophagus. FIG. 11A is an explanatory diagram showing an encapsulated medical device of a variant that has a linkage hole formed obliquely with respect to the longitudinal axis of the device. FIG. 11B is an explanatory diagram showing an encapsulated medical device of a variant that has a linkage hole formed to be tortuous with respect to the longitudinal axis of the device. FIG. 12A is an explanatory diagram showing the appearance of an encapsulated medical device of a variant that has a plurality of projections formed on the periphery of a capsule body thereof. FIG. 12B shows the appearance of the front part of the encapsulated medical device shown in FIG. 12A.

As shown in FIG. 1, an encapsulated medical device 1 transmits or receives radio waves to or from an extracorporeal device 3 while passing through the lumen of a body cavity of a patient 2. The encapsulated medical device 1 can examine, cure, or treat an internal region under the control of the extracorporeal device 3. The encapsulated medical device 1 and extracorporeal device 3 constitute a medical system 4.

The medical system 4 is designed to examine the esophagus, duodenum, small intestine, or large intestine according to a method described below. For example, the method of a screening of the esophagus, duodenum, small intestine, or large intestine is performed such that the encapsulated medical device 1 is, like a medicine, swallowed together with water or the like after the completion of pretreatment for, for example, the large intestine (intestinal cleansing). If the medical system 4 is used to deal with the esophagus or the like, the encapsulated medical device 1 quickly passes through the esophagus. In this case, the esophagus is visualized at a rate of 10 frames per sec. If the medical system 4 is used to deal with the small intestine or the like, the encapsulated medical device 1 slowly passes through the small intestine. In this case, the small intestine is visualized at a rate of two frames per sec. The picked up images are subjected to required signal processing and digital compression, transferred to the extracorporeal device 3, and then recorded. Consequently, required information alone can be visualized in the form of a motion picture in order to facilitate diagnosis.

To begin with, the extracorporeal device 3 will be described.

The extracorporeal device 3 consists mainly of a personal computer 11, a keyboard 12, a monitor 13, and an extracorporeal antenna 14. The personal computer 11 has the function to control the encapsulated medical device 1. The keyboard 12 is connected to the personal computer 11 and used to enter commands or data. The monitor 13 is connected to the personal computer 11 and serves as a display means for displaying images or the like. The extracorporeal antenna 14 is connected to the personal computer 11, sends a control signal that is used to control the encapsulated medical device 1, and receives a signal sent from the encapsulated medical device 1.

The extracorporeal device 3 produces a control signal, which is used to control the encapsulated medical device 1, by pressing the key-entry on the keyboard 12 or by using a control program stored on a hard disk incorporated in the personal computer 11. In the extracorporeal device 3, the produced control signal is transferred to a transmission circuit incorporated in the personal computer 11, modulated using a carrier of a predetermined frequency, and transmitted in the form of a radio wave through the extracorporeal antenna 14.

The encapsulated medical device 1 receives the radio wave through a radio antenna 21 that will be described later, demodulates the control signal carried by the radio wave, and outputs the control signal to respective circuits.

Moreover, the extracorporeal device 3 receives through the extracorporeal antenna 14 information (data) signals such as a video signal which are sent from the encapsulated medical device 1 through the radio antenna 21. The information signal is then transferred to the monitor 13 to display the image.

Next, the components of the encapsulated medical device 1 in accordance with the present embodiment will be detailed in conjunction with FIG. 2 and FIG. 3A to FIG. 3C.

The encapsulated medical device of the present embodiment is designed exclusively for examination (observation) use.

The encapsulated medical device 1 consists mainly of the radio antenna 21, a radio transmission/reception circuit 22, an illuminator 23, an observation unit 24, a digital signal processing circuit 25, a battery unit 26, and a switch 27. Radio waves are transmitted or received to or from the extracorporeal device 3 through the radio antenna 21. The radio transmission/reception circuit 22 processes signals of a radio wave that is transmitted or received through the radio antenna 21. The illuminator 23 is composed of light-emitting diodes (LEDs) that generate illumination light with which the lumen of a body cavity is illuminated. The observation unit 24 picks up an optical image of a body cavity illuminated with the illumination light emanating from the illuminator 23. The digital signal processing circuit 25 digitally processes an image signal produced by the observation unit 24. A battery 26a that includes cells and delivers supply power is placed in the battery unit 26. The switch 27 is turned on or off in order to put the supply power, which is delivered from the battery unit 26, to an on-state or off-state level.

The radio transmission/reception circuit 22 selectively samples a carrier that is a radio wave received from the extracorporeal device 3 through the radio antenna 21, detects the waveform of a control signal, and demodulates the control signal. The control signal is then transferred to respective circuits. Moreover, the radio transmission/reception circuit 22 modulates information (data) signals including a video signal and being sent from the circuits by using a carrier of a predetermined frequency, and transmits the carrier in the form of a radio wave through the radio antenna 21.

The observation unit 24 includes an objective optical system 31, an image pickup sensor 32, and an image pickup drive circuit 33. The objective optical system 31 forms an optical image. The image pickup sensor 32 includes a complementary metal oxide semiconductor (CMOS) and picks up the optical image formed by the objective optical system 31. The image pickup drive circuit 33 drives the image pickup sensor 32.

The digital signal processing circuit 25 includes a digital video signal processing circuit (hereinafter, a video signal processing circuit) 34 and a digital compression circuit (hereinafter, a compression circuit) 35. The video signal processing circuit 34 processes an image signal produced by the image pickup sensor 32 and converts it into a digital video signal. The compression circuit 35 compresses the digital video signal produced by the video signal processing circuit 34.

The battery unit 26 delivers supply power from the battery 26a placed therein to the illuminator 23, digital signal processing circuit 25, and radio transmission/reception circuit 22 via the switch 27. The supply power delivered from the battery 26a is routed to the observation unit 24 via the digital signal processing circuit 25.

Moreover, the encapsulated medical device 1 has a permanent magnet (hereinafter, simply, a magnet) 36 incorporated therein. The magnet is needed in order to recover the encapsulated medical device, which comes to a standstill in the lumen of a body cavity, using a string-like recovering tool that has a magnet included in the front part thereof and that will be described later (see FIG. 7).

As shown in FIG. 3A to FIG. 3C, the encapsulated medical device 1 includes a cylindrical capsule body 1A that can be passed through the lumen of a body cavity in order to examine, cure, or treat an internal region of the body cavity and that is sealed to be airtight using a transparent body armor member 41. The encapsulated medical device 1 has built-in components, which include the aforesaid illuminator 23 and observation unit 24, placed in the capsule body 1A. To be more specific, the encapsulated medical device 1 has the objective optical system 31, which is included in the observation unit 24, placed in the center of the front part of the capsule body 1A. Moreover, the encapsulated medical device 1 has the image pickup sensor 32 disposed at the position of the image plane of the objective optical system 31.

The image pickup drive circuit 33 encircles the image pickup sensor 32. The digital signal processing circuit 25 is disposed proximally to the image pickup drive circuit 33 and image pickup sensor 32. The radio transmission/reception circuit 22 is disposed proximally to the digital signal processing circuit 25.

The illuminators 23 are disposed at the periphery of the objective optical system 31, and illuminates a point in front of the capsule body 1A via the body armor member 41. In the drawing, the illuminator 23 is composed of, for example, four LEDs.

The battery unit 26 is located behind the radio transmission/reception circuit 22. The battery 26a composed of, for example, three cells is stored in the battery unit 26. If the switch 27 is pressed, the battery unit 26 delivers supply power via the switch 27. The radio antenna 21 as well as the magnet 36 is disposed behind the battery unit 26.

The encapsulated medical device 1 has the aforesaid built-in components held in the body armor member 41 while being reinforced and borne by a metallic ring reinforcement member that is not shown. The encapsulated medical device 1 is designed to have a size permitting the patient 2 to swallow the capsule body 1A easily.

In the present embodiment, the capsule body 1A has an extended portion 42. The extended portion 42 is formed at one end of one axis of the cross section of the capsule body 1A cut at right angle to the longitudinal axis thereof, such that the cross section of the capsule body 1A is non-circular. Herein, provided that the capsule body 1A does not have the extended portion 42, the cross section of the capsule body 1A is substantially circular. The capsule body 1A not only has the extended portion 42 that serves as fluid passage forming means but also a linkage hole 43 that serves as a fluid passage that allows a fluid such as a gas or humor to flow forwards or backwards in a lumen. Consequently, when the capsule body 1A comes into close contact with the internal surface of a body cavity to block the lumen of the body cavity, a fluid such as a gas or humor flows forwards or backwards in the lumen through the linkage hole 43.

Next, actions to be performed in the encapsulated medical device 1 of the present embodiment will be described below.

As shown in FIG. 1, when the lumen of a body cavity of the patient 2, for example, the lumen of a stomach 51 thereof must be observed for a prolonged period of time, an operator asks the patient 2 to swallow the encapsulated medical device 1. Thus, the encapsulated medical device 1 passes through the lumen of the stomach 51. At this time, immediately before the patient 2 swallows the encapsulated medical device 1, the operator turns on the switch 27 of the encapsulated medical device 1. Consequently, supply power is delivered from the battery 26a in the battery unit 26 to the illuminator 23, observation unit 24, digital signal processing circuit 25, and radio transmission/reception circuit 22 respectively.

The encapsulated medical device 1 passes through an oral cavity 52, descends an esophagus 53, and enters the stomach 51. At this time, as shown in FIG. 4, the major axis of the cross section of the esophagus 53 is approximately 16 mm long and the minor axis thereof is approximately 14 mm long. The encapsulated medical device 1 can therefore pass through the esophagus readily.

If the lumen of the stomach 51 must be observed, an operator makes key-entry at, for example, the keyboard 12 included in the extracorporeal device 3 so as to input an observation start command. Consequently, a control signal produced responsively to the key-entry is radiated in the form of a radio wave through the extracorporeal antenna 14 and thus transmitted from the extracorporeal device 3 to the encapsulated medical device 1.

The encapsulated medical device 1 detects an operation start signal in the signal received through the radio antenna 21. Consequently, the radio transmission/reception circuit 22, illuminator 23, observation unit 24, and digital signal processing circuit 25 are driven.

The illuminator 23 emits illumination light towards a field of view offered by the observation unit 24. An optical image of an illuminated region falling within the field of view is picked up by the image pickup sensor 32 included in the observation unit 24, and photoelectrically converted into an image signal. The picked-up image signal is converted into a digital video signal by the video signal processing circuit 34 included in the digital signal processing circuit 25, compressed by the compression circuit 35, and modulated by the radio transmission/reception circuit 22. The resultant signal is radiated in the form of a radio wave through the radio antenna 21.

The extracorporeal device 3 receives the radio wave through the extracorporeal antenna 14. The received radio wave is demodulated by a receiving circuit included in the personal computer 11 and converted into a digital signal by an A/D converter included in the personal computer 11. The resultant digital signal is stored in a memory and read at a predetermined rate. Consequently, the picked-up optical image is displayed in colors on the monitor 13. The operator views the image so as to observe the lumen of the stomach 5 of the patient 2. The optical image may be recorded in an image recording device that is not shown.

After the observation of the stomach 51 is completed, the encapsulated medical device 1 is inched outwards from the stomach 51, and taken out through the anus, which is not shown, by way of a duodenum 54, small intestine 55, and large intestine 56. Meanwhile, the encapsulated medical device 1 permits observation of the lumen of the alimentary canal.

At this time, the encapsulated medical device 1 may, as shown in FIG. 5, come to a standstill in a stenosed part 55a of the lumen of the small intestine 55. In this case, as shown in FIG. 6, the encapsulated medical device 1 comes into close contact with the internal surface of the small intestine in the stenosed part 55a of the small intestine 55 to block the lumen thereof.

In this case, the encapsulated medical device 1 must be, as shown in FIG. 7, recovered using a string-like recovering tool 60.

However, it takes much time to recover the encapsulated medical device 1 using the string-like recovering tool 60. Meanwhile, a conventional encapsulated medical device fails to allow a fluid 61 such as a gas or humor to flow forwards or backwards beyond the stenosed part 55a of the small intestine 55 in the lumen thereof.

In the encapsulated medical device 1 of the present embodiment, the linkage hole 43 is bored as a fluid passage in the extended portion 42. The fluid 61 such as a gas or humor can therefore flow forwards or backwards beyond the stenosed part 55a of the small intestine 55 in the lumen thereof. The encapsulated medical device 11 is then recovered using the sting-like recovering tool 60.

Consequently, if the encapsulated medical device 1 of the present invention comes to a standstill in a deep region in the lumen of a body cavity such as the small intestine 55 for a prolonged period of time, the fluid 61 such as an intestinal gas or humor can flow forwards or backwards in the lumen. Nevertheless, the ease of swallowing does not deteriorate.

Moreover, an encapsulated medical device may have a linkage groove formed, as shown in FIG. 8A to FIG. 8C, in the extended portion 42 of the capsule body 1A on behalf of the linkage hole 43.

As shown in FIG. 8A to FIG. 8C, an encapsulated medical device 71 has a linkage groove 73 formed in an extended portion 72 of a capsule body 71A.

The extended portion 72 has chamfers 74 formed on the banks of the linkage groove 73. Consequently, even when the extended portion 72 comes into close contact with the internal surface of a body cavity, the extended portion 72 safely protects the internal surface.

Similarly to the encapsulated medical device 1, when the encapsulated medical device 71 comes into close contact with the internal surface of a body cavity to block the lumen of the body cavity, a fluid such as a gas or humor flows forwards or backwards in the lumen through the linkage groove 73. The other components are identical to those of the encapsulated medical device 1, and the description of the components will therefore be omitted.

Consequently, the encapsulated medical device 71 provides the same advantages as the aforesaid encapsulated medical device 1.

Moreover, an encapsulated medical device may be designed so that the center axis thereof passing the center of the minor axis of the cross section thereof cut at right angle to the longitudinal axis thereof will be, as shown in FIG. 9A and FIG. 9B, deviated from the optical axis of the observation unit 24.

As shown in FIG. 9A and FIG. 9B, an encapsulated medical device 81 is designed so that a center axis 82 of a capsule body 81A passing the center of the minor axis of the cross section thereof cut at right angle to the longitudinal axis thereof is deviated from the optical axis 83 of the observation unit 24.

Moreover, the encapsulated medical device 81 has linkage holes 43 bored in an extended portion 84 that is disposed on the side of the optical axis 83 of the observation unit 24 opposite to the center axis 82 passing the center of the cross section cut at right angle to the longer axis. As for the linkage holes 43, for example, three linkage holes are formed symmetrically to one another with respect to the major axis 85 of the cross section. The linkage holes 43 may be replaced with linkage grooves 73.

Consequently, the encapsulated medical device 81 can be designed to permit slightly oblique vision with the optical axis of the observation unit 24 tilted relative to the center axis 82 passing the center of the minor axis of the cross section of the device cut at right angle to the longitudinal axis direction thereof.

Moreover, an encapsulated medical device may include a capsule body that has, as shown in FIG. 10A and FIG. 10B, extended portions formed at both ends of one axis of the cross section thereof.

As shown in FIG. 10A and FIG. 10B, an encapsulated medical device 91 includes a capsule body 91A that has an upper extended portion 92 and a lower extended portion 93 formed at both ends of one axis of the cross section thereof. Consequently, the cross section of the capsule body cut at right angle to the longitudinal axis thereof is elliptic. FIG. 10B shows the encapsulated medical device 91 passing through the esophagus 53. Since the cross section of the esophagus 53 is elliptic, the encapsulated medical device 91 can readily pass through the esophagus.

The encapsulated medical device 91 has the linkage groove 73 formed in the upper extended portion 92 and the linkage hole 43 formed in the lower extended portion 93. The linkage groove 73 and linkage hole 43 are substantially symmetrically to each other with respect to the minor axis 94 of the cross section of the encapsulated medical device. Alternatively, the encapsulated medical device 91 may have the linkage hole 43 formed in the upper extended portion and the linkage groove 73 formed in the lower extended portion 93. Otherwise, the linkage hole 43 or linkage groove 73 may be formed in each of the upper and lower extended portions 92 and 93. The encapsulated medical device 91 may have a plurality of linkage grooves 73 or linkage holes 43 formed symmetrically to one another with respect to the major axis 95 of the cross section thereof at the ends of which the upper and lower extended portions 92 and 93 are formed.

Moreover, the encapsulated medical device 91 may have various types of sensors disposed on the periphery of the capsule body 91A in such a manner that the sensing portions of the sensors are exposed to outside and the interior of the device is kept watertight.

The encapsulated medical device 91 has an optical sensor 96, which detects the brightness of the interior of a living body, disposed on the periphery of the tip of the capsule body 91A. The encapsulated medical device 91 includes a pH sensor 97 and a temperature sensor 98 disposed on the periphery of the back of the capsule body 91A. The pH sensor 97 detects a chemical quantity (pH) of an intracavitary juice, and the temperature sensor 98 detects the temperature of each organ. Various types of sensors may include, in addition to the optical sensor 96, pH sensor 97, and temperature sensor 98, a pressure sensor that detects the pressure applied from the internal surface of a lumen to the external surface of the capsule body 91A during passage of the capsule body through the lumen, and a hemoglobin sensor that detects an amount of hemoglobin in each organ (whether each organ is bleeding).

Information (data) acquired by the sensing portion of each of the various types of sensors is temporarily stored in a memory, which is not shown, in the capsule body 91A. Thereafter, the information (data) is modulated by the radio transmission/reception circuit 22 in the same manner as it is described in relation to the encapsulated medical device 1, and radiated in the form of a radio wave through the radio antenna 21. The radio wave is received by the extracorporeal device 3 through the extracorporeal antenna 14, demodulated by a reception circuit included in the personal computer 11, and temporarily stored as information (data) in the memory. Thereafter, the information (data) stored in the memory is compared with a reference value stored in advance in the memory by a central processing unit (CPU) included in the personal computer 11. The result of comparison is displayed on the monitor 13. Consequently, an operator such as a doctor or a co-medical can judge whether an abnormality such as a disease or bleeding is found or a position or state at or in which the capsule body passes.

In particular, the encapsulated medical device 91 permits judgment of an alimentary disease or physiological analysis thereof when designed to measure a pH or an amount of hemoglobin in the alimentary canal of a living body. The encapsulated medical device 91 is therefore very useful. When a plurality of types of sensors are included as various types of sensors in the encapsulated medical device 91, examinations can be achieved efficiently.

Moreover, an encapsulated medical device may be, as shown in FIG. 11A and FIG. 11B, designed so that the linkage hole 43 will intersect the longitudinal axis of the device but not be parallel with the longitudinal axis.

As shown in FIG. 11A, an encapsulated medical device 101 has the linkage hole 43 formed in a capsule body 101A slightly obliquely with respect to the longitudinal axis 102 of the capsule body 101A but not in parallel with the longitudinal axis 102. Moreover, as shown in FIG. 11B, an encapsulated medical device 103 has the linkage hole 43 formed in a capsule body 103A to be tortuous but not be parallel with the longitudinal axis 102.

The encapsulated medical devices 101 and 103 shown in FIG. 11A and FIG. 11B each have a distal opening 43*a* bored in the front part of the capsule body 101A or 103A and a back opening 43*b* bored in the back part thereof. The distal opening 43*a* and back opening 43*b* serve as the entrances or exits of the linkage hole 43.

Moreover, an encapsulated medical device may be, as shown in FIG. 12A and FIG. 12B, designed to have a plurality of projections formed on the periphery of a capsule body so as to form a fluid passage.

Specifically, as shown in FIG. 12A and FIG. 12B, an encapsulated medical device 110 has a plurality of projections 111 formed on the periphery of a capsule body 110A. Consequently, when the encapsulated medical device 110 comes into close contact with the internal surface of the small intestine 55 in a stenosed part 55*a* thereof to block the lumen of the small intestine, the fluid 61 such as a gas or humor can flow forwards or backwards beyond the stenosed part 55*a* of the small intestine by way of concave parts 111*a* formed among the plurality of projections 111. Herein, reference numeral 112 denotes a projection type pressure sensor whose sensing portion is a projection. The pressure sensors 112 are used to detect pressures, whereby the fact that the encapsulated medical device 110 has blocked, for example, the lumen of the small intestine 55 is sensed.

Moreover, the encapsulated medical device 110 is designed to spray a medicine. Specifically, the encapsulated medical device 110 has a medicine spray opening 113*a* bored in the front part thereof so that a medicine preserved in a medicine reservoir 113 in the capsule body 110A can be sprayed.

Furthermore, the encapsulated medical device 110 is designed to sample a humor. Specifically, the encapsulated medical device 110 has a humor infusion opening 114*a* bored in the back part thereof so that a humor can be sampled and infused into a humor reservoir 114 in the capsule body 110A. Opening or closing the openings 113*a* and 114*a* is controlled by the extracorporeal device 3 over a communication link in the same manner as described in relation to the first embodiment. Consequently, the encapsulated medical device 110 can discharge the medicine from the medicine reservoir 113 and spray it through the medicine spray opening 113*a* in an intended region. Moreover, a humor can be sampled and infused into the humor reservoir 114 through the humor infusion opening 114*a*.

Incidentally, the encapsulated medical device 110 may be designed to be able to mix a medicine in the medicine reservoir 113 with a humor sampled through the humor infusion opening 114*a*, discharge the mixture through the medicine spray opening 113*a*, and thus spray the mixture.

According to the present embodiment, the present invention is implemented in an encapsulated medical device that has the radio antenna 21 through which data is transmitted or received to or from the extracorporeal device 3, and that is passed through the lumen of a body cavity in order to examine, cure, or treat an internal region of the body cavity under the control of the extracorporeal device 3. The present invention is not limited to this type of encapsulated medical device. The present invention may be implemented in an encapsulated medical device that does not have the radio antenna 21 and that is passed through the lumen of a body cavity and then recovered in order to obtain information (data) of the optical image and the like, outside the living body.

Second Embodiment

Figure 15:
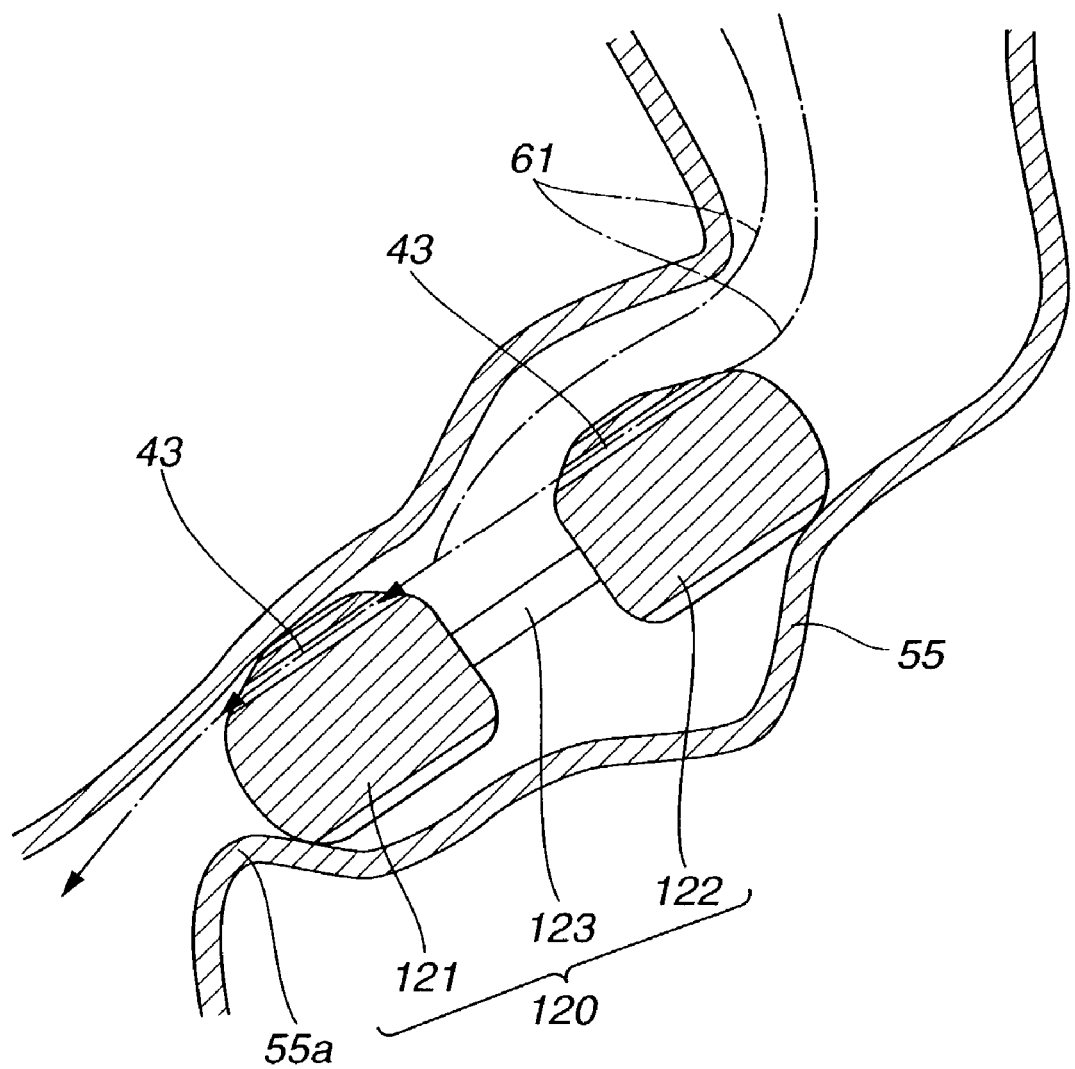
FIG. 15 is a sectional view showing a scene where the encapsulated medical device shown in FIG. 13A to FIG. 14 has come to a standstill in a stenosed part of the small intestine.

FIG. 13A to FIG. 15 are concerned with a second embodiment of the present invention. FIG. 13A is a sectional view showing the components of an encapsulated medical device in accordance with the second embodiment of the present invention. FIG. 13B is an A—A sectional view of the encapsulated medical device shown in FIG. 13A. FIG. 13C is a B—B sectional view of the encapsulated medical device shown in FIG. 13A. FIG. 13D is a C—C sectional view of the encapsulated medical device shown in FIG. 13A. FIG. 14 is a D—D sectional view of the encapsulated medical device shown in Fig. B. FIG. 15 is a sectional view showing a scene where the encapsulated medical device shown in FIG. 13A to FIG. 14 has come to a standstill in a stenosed part of the small intestine.

In the aforesaid first embodiment, the encapsulated medical device is formed with one capsule body. In the second embodiment, a capsule body is divided into a distal hard member and a back hard member. The distal hard member and back hard member are linked with a flexible string-like member. The other components are nearly identical to those of the first embodiment. The description of the components will be omitted, and the same reference numerals will be assigned to the components.

As shown in FIG. 13A to FIG. 13C, an encapsulated medical device 120 of the second embodiment has a capsule body thereof composed of a distal hard member 121 and a back hard member 122 that are linked by a flexible string-like member 123.

The distal hard member 121 and back hard member 122 are, similarly to the capsule body of the encapsulated medical device of the first embodiment, shaped like cylinders and covered with a transparent body armor member 41 to be kept airtight. Each of the distal hard member 121 and back hard member 122 has an extended portion 124 formed at the upper end of one axis of the cross section thereof cut at right angle to the longitudinal axis thereof. The cross section of each of the distal hard member 121 and back hard member 122 is non-circular, though the cross section thereof without the extended portion 124 is substantially circular.

The distal hard member 121 has, similarly to the capsule body of the encapsulated medical device 1 of the first embodiment, the observation unit 24, illuminator 23, digital signal processing circuit 25, and radio transmission/reception circuit 22 placed therein. The distal hard member 121 has the radio antenna 21 disposed in the center of the extended portion 124.

As shown in FIG. 14, the extended portion 124 of the distal hard member 121 has the linkage holes 43, which serve as a fluid passage, formed across the radio antenna 21. In contrast, the back hard member 122 has the battery unit 26 placed therein. The switch 27 to be turned on or off in order to put supply power, which is delivered from the battery unit 26, to an on-state or off-state level is disposed in the center of the extended portion 124. Moreover, the back hard member 122 has the magnet 36 placed in the back part thereof. In the extended portion 124 of the back hard member 122, the linkage holes 43 serving as a fluid passage are formed across the switch 27.

The string-like member 123 is formed with an armor watertight member such as a urethane tube. The string-like member 123 is structured so that electric cables 123a led out from the battery unit 26 in the back hard member 122 can run through the string-like member 123 and supply power delivered from the battery unit 26 can be routed to the distal hard member 121. Referring to FIG. 13D, the number of electric cables 123a is four so that the electric cables 123a will lead to the observation unit 24, illuminator 23, digital signal processing circuit 25, and radio transmission/reception circuit 22 respectively.

The encapsulated medical device 120 of the second embodiment having the foregoing components is, similarly to the encapsulated medical device 1 described as the first embodiment, swallowed by the patient 2 for use.

The encapsulated medical device 120 passes through the oral cavity 52, descends the esophagus 53, and enters the stomach 51. The encapsulated medical device 120 then captures images in the lumen of the stomach 51 using the image pickup sensor 32. The image data is radiated in the form of a radio wave through the radio antenna 21. Consequently, the images are displayed on the monitor of the extracorporeal device 3.

Thereafter, assume that the encapsulated medical device 120 comes to a standstill in the stenosed part 55a of, for example, the small intestine 55 and comes into close contact with the internal surface of the small intestine to block the lumen of the small intestine.

Nevertheless, as far as the encapsulated medical device 120 of the second embodiment is concerned, the linkage holes 43 are bored as a fluid passage in the extended portions 12. The fluid 61 such as a gas or humor can flow forwards or backwards beyond the stenosed part 55a of the small intestine 55 in the lumen of the small intestine. Thereafter, the encapsulated medical device 120 is recovered using the string-like-recovering tool 60 in the same manner as it is described in relation to the first embodiment.

Consequently, the encapsulated medical device 120 of the present embodiment provides the same advantages as the one of the first embodiment. Furthermore, according to the present embodiment, an encapsulated medical device can be designed more compactly.

Third Embodiment

Figure 21A:
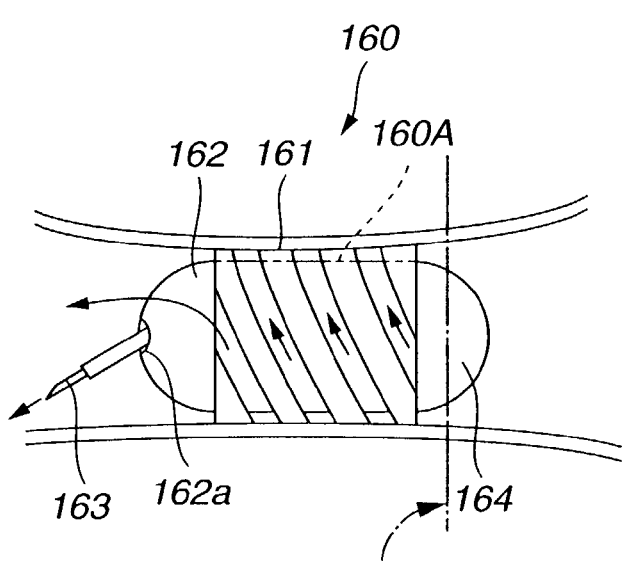
FIG. 21A is an explanatory diagram showing an encapsulated medical device of a variant that has an elastic rubber cover, which has a spiral groove formed therein and serves as an armor member, freely detachably attached to a capsule body thereof.
Figure 21B:
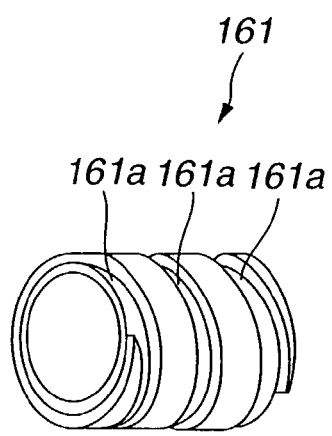
FIG. 21B is a perspective view showing the elastic rubber cover shown in FIG. 21A.
Figure 16:
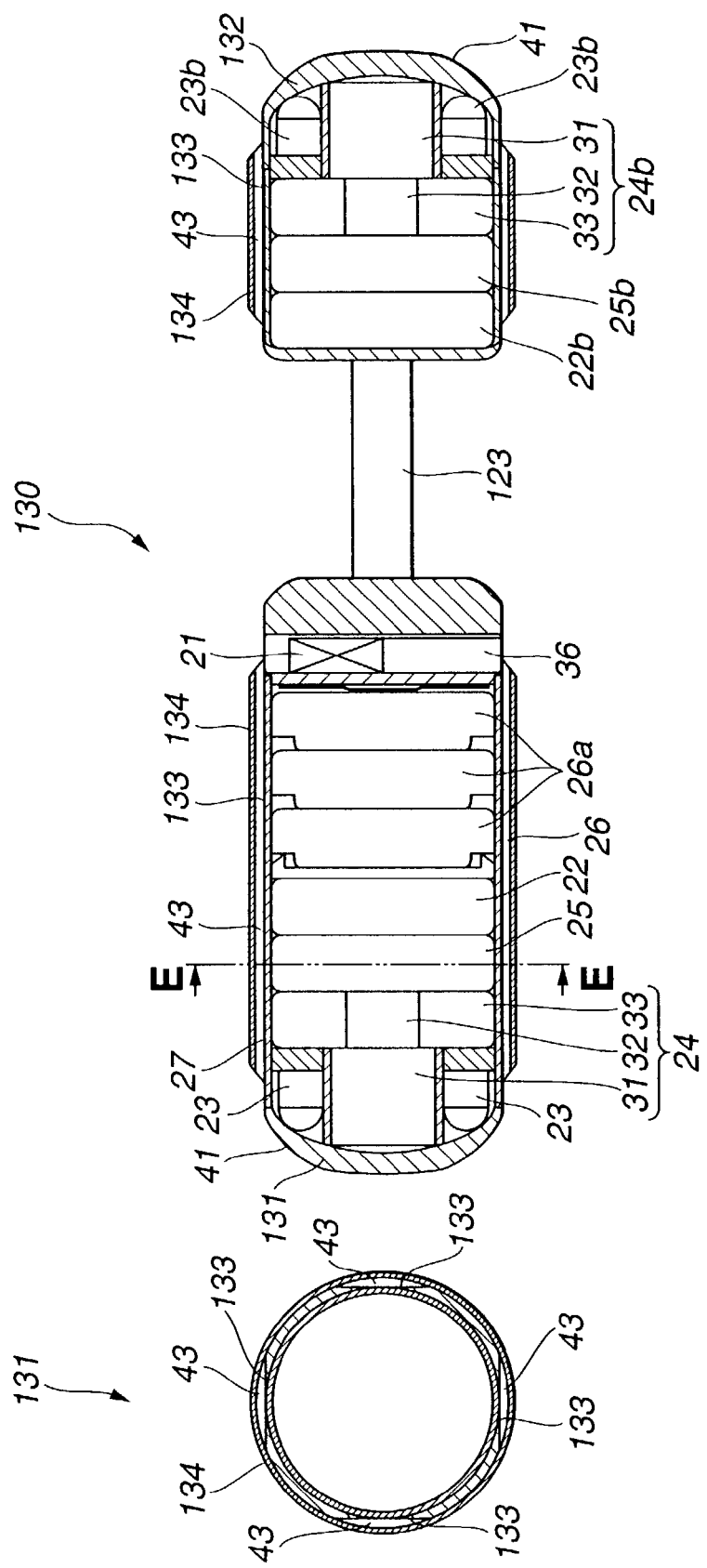
FIG. 16A is a sectional view showing the components of an encapsulated medical device in accordance with a third embodiment of the present invention.
FIG. 16B is an E—E sectional view of the encapsulated medical device shown in FIG. 16A.
Figure 17:
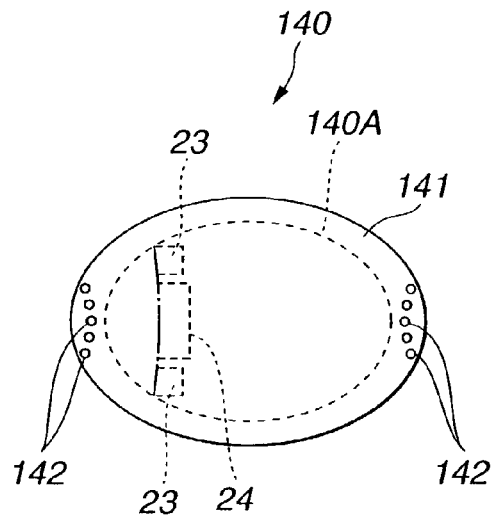
FIG. 17 is an explanatory diagram showing an encapsulated medical device of a variant that has a capsule body thereof covered with a transparent member that is an armor member.
Figure 19:
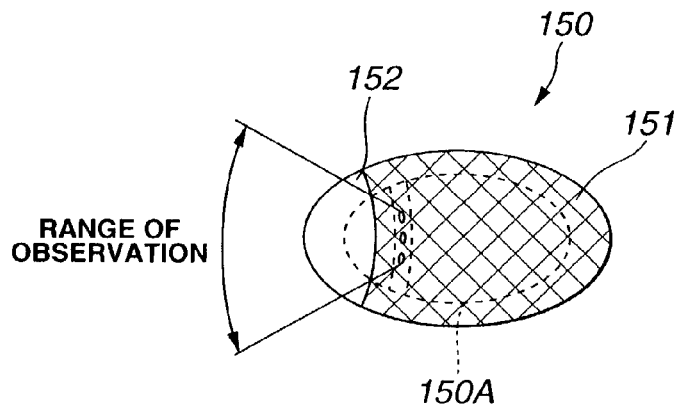
FIG. 19 is an explanatory diagram showing an encapsulated medical device of a variant that has a net-like mesh cover (mesh jacket) serving as an armor member freely detachably attached to a capsule body thereof.
Figure 20:
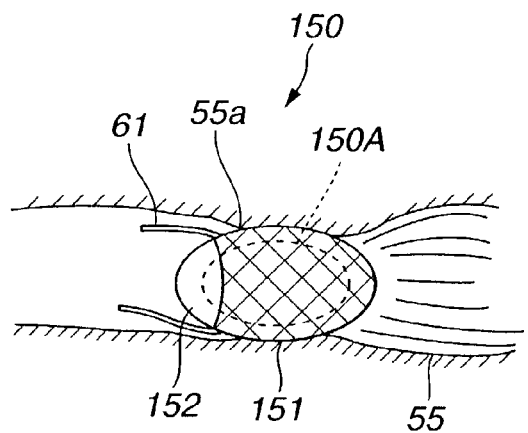
FIG. 20 is an explanatory diagram showing a scene where the encapsulated medical device shown in FIG. 19 has come to a standstill in a stenosed part of the small intestine.

FIG. 16A to FIG. 21B are concerned with a third embodiment of the present invention. FIG. 16A is a sectional view showing the components of an encapsulated medical device in accordance with the third embodiment of the present invention. FIG. 16B is an E—E sectional view of the encapsulated medical device shown in FIG. 16A. FIG. 17 is an explanatory diagram showing an encapsulated medical device of a variant that has a capsule body thereof covered with a transparent member that is an armor member. FIG. 18 is an explanatory diagram showing a scene where the encapsulated medical device shown in FIG. 17 has come to a standstill in a stenosed part of the small intestine. FIG. 19 is an explanatory diagram showing an encapsulated medical device of a variant that has a net-like mesh cover (mesh jacket) freely detachably attached to a capsule body thereof. FIG. 20 is an explanatory diagram showing a scene where the encapsulated medical device shown in FIG. 19 has come to a standstill in a stenosed part of the small intestine. FIG. 21A is an explanatory diagram showing an encapsulated medical device of a variant that has an elastic rubber cover, which serves as an armor member and has a spiral groove formed therein, freely detachably attached to a capsule body thereof. FIG. 21B is a perspective view showing the elastic rubber cover shown in FIG. 21A.

In the first and second embodiments, the linkage hole 43 or linkage groove 73 that is a fluid passage is formed in an extended portion of a capsule body that serves as fluid passage forming means. In the third embodiment, a fluid passage can be formed in an armor member that is freely detachably attached to the periphery of a capsule body and that serves as fluid passage forming means. The other components are nearly identical to those of the first or second embodiment. The same reference numerals will be assigned to the components, and the description of the components will be omitted.

As shown in FIG. 16A and FIG. 16B, an encapsulated medical device 130 of the third embodiment has a capsule body, which accommodates nearly the same built-in components as those described in relation to the first embodiment, as a distal hard member 131. The distal hard member 131 and a back hard member 132 are linked using a string-like member 123.

The distal hard member 131 does not have, unlike the capsule body described as a component of the first embodiment, the extended portion 42. Instead, the distal hard member 131 has notches 133 that are located at the top and bottom of a substantially circular cross section of the distal hard member 131, and the right and left sides of the cross section. A hard tubular member 134 that is an armor member is freely detachably attached to the periphery of the distal hard member 131, whereby the linkage holes 43 are formed between the internal surface of the hard tubular member 134 serving as fluid passage forming means and the notches 133.

On the other hand, the back hard member 132 has, similarly to the distal hard member 131, a tubular member 134, which serves as a fluid passage forming member, freely detachably attached to the periphery thereof in which the notches 133 are formed. Thus, the linkage holes 43 are formed.

Moreover, the back hard member 132 faces in a direction opposite to a direction in which the distal hard member 131 faces, thus permitting observation of the backward part of the lumen of a body cavity which lies in a direction opposite to a direction of advancement. A back-side illuminator 23b, a back-side observation unit 24b, a back-side digital signal processing circuit 25b, and a back-side radio transmission/reception circuit 22b are placed in the back hard member 132. Supply power is delivered from the battery unit 26 included in the distal hard member to the back hard member 132 by way of the string-like member 123.

In the back hard member 132, the back-side radio transmission/reception circuit 22b detects a signal, which is received by the distal hard member 131 through the radio antenna 21, by way of the string-like member 123. Responsively to the detection of the signal, the back-side illuminator 23b, back-side observation unit 24b, and back-side digital signal processing circuit 25b are driven.

In the back hard member 132, the back-side radio transmission/reception circuit 22b modulates video data which the back-side observation unit 24 produces by picking up an optical image. Consequently, the video data is transferred to the distal hard member 131 by way of the string-like member 123 and radiated in the form of a radio wave through the radio antenna 21. Incidentally, the distal and back hard members 131 and 132 included in the encapsulated medical device 130 may be realized with a sole unit similarly to the capsule body included in the first embodiment.

Consequently, the encapsulated medical device 130 of the third embodiment provides the same advantages as the second embodiment. In addition, a view of a backward region can be produced.

Moreover, an encapsulated medical device may have a capsule body thereof covered with, as shown in FIG. 17, a transparent member that is an armor member.

Specifically, an encapsulated medical device 140 has, as shown in FIG. 17, a capsule body 140A thereof covered with a transparent plastic armor member 141.

The armor member 141 encloses the periphery of the capsule body 140A with a gap between them. A plurality of through-holes 142 that open into the gap and serve as linkage holes are bored in each of the distal and back parts of the capsule body 140A. Consequently, the encapsulated medical device 140 allows the fluid 61 such as a gas or humor to flow into the gap through the through-holes 142 and then flow out of the distal or back part thereof through the through-holes 142. The components of the capsule body 140A are identical to those of the distal hard member 131 described in conjunction with FIG. 16A and FIG. 16B. The description of the components will therefore be omitted.

When the encapsulated medical device 140 having the foregoing components blocks the lumen of, for example, the small intestine 55 in the stenosed part 55a thereof, the fluid 61 such a humor can pass the stenosed part 55a to flow forwards or backwards.

Moreover, an encapsulated medical device may be, as shown in FIG. 19, designed to have a net-like mesh cover (mesh jacket), which serves as an armor member, freely detachably attached to a capsule body thereof.

Specifically, as shown in FIG. 19, an encapsulated medical device 150 has a mesh cover (mesh jacket) 151 freely detachably attached to a capsule body 150A. Consequently, the encapsulated medical device 150 allows the fluid 61 such as a gas or humor to flow into the distal and back ends thereof through the small holes in the mesh cover 151 that serve as linkage holes.

At least a portion of the capsule body 150A falling within a range of observation offered by the observation unit 24 included in the capsule body 150A is covered with a transparent plastic cover 152 but not with the mesh cover 151.

When the encapsulated medical device 150 having the foregoing components comes into, as shown in FIG. 20, close contact with the internal surface of the small intestine 55 in the stenosed part 55a thereof to block the lumen thereof, the encapsulated medical device 150 allows the fluid 61 such as a humor to pass the stenosed part 55a so as to flow forwards or backwards.

Moreover, an encapsulated medical device may be, as shown in FIG. 21A and FIG. 21B, designed to have an elastic rubber cover, which has a spiral groove formed therein and serves as an armor member, freely detachably attached to a capsule body. Specifically, as shown in FIG. 21A and FIG. 21B, an encapsulated medical device 160 has an elastic rubber cover 161, which has a spiral groove 161a formed as a linkage groove therein, freely detachably attached to a capsule body 160A. Consequently, the encapsulated medical device 160 allows the fluid 61 such as a gas or humor to flow out of the distal or back part thereof through the spiral groove 161a formed in the elastic rubber cover 161.

Moreover, the encapsulated medical device 160 has a treatment appliance storage 162 included in the capsule body 160A so as to enable cure or treatment. A treatment appliance opening 162a is bored in the front part of the treatment appliance storage 162. The treatment appliance opening 162a is filled up with a soluble membrane made of gelatin that is digested with a gastric juice or a fatty acid membrane that is digested with an intestinal juice. When the encapsulated medical device 160 reaches a region near an intended region, the treatment appliance opening 162a opens.

The front part of a treatment appliance 163 contained in the treatment appliance storage 162 can freely project or sink through the treatment appliance opening 162a. Therefore, an intended region in the lumen of a body cavity can be cured or treated. The movement of the treatment appliance 163 is controlled by the extracorporeal device 3 over a communication link as described in relation to the first embodiment. In practice, the movement of the treatment appliance 163 may be controlled using a joystick that is not shown and that is connected to the personal computer 11.

In FIG. 21A, the treatment appliance 163 is an injection needle through which a hemostyptic can be injected. In this case, after a bleeding region is identified using a blood sensor that is not shown or the observation unit 24, the encapsulated medical device 160 instructs the movement of the treatment appliance 163 such as the hemostyptic injection needle stored in the capsule body 160A while being controlled by the extracorporeal device 3 over a communication link. Consequently, ethanol or any other powder that is a hemostyptic is sprayed to the bleeding region in order to arrest the bleeding.

Moreover, the encapsulated medical device 160 has an ultrasonic unit 164 included in the capsule body so that an ultrasonic examination can be performed.

The ultrasonic unit 164 consists of an ultrasonic probe that transmits or receives ultrasonic waves, and an ultrasound control circuit that controls or drives the ultrasonic probe, though the ultrasonic probe and ultrasound control circuit are not shown.

The encapsulated-medical device 160 has the ultrasonic probe kept watertight so that an acoustic lens that is not shown will be embedded in the external surface of the back part of the capsule body 160A. An ultrasonic tomographic image of a plane that extends 360° around the back part of the capsule body 160A can be produced.

In the encapsulated medical device 160, the data of the produced ultrasonic tomographic image is modulated by the radio transmission/reception circuit 22 in the same manner as view image data is modulated as described in relation to the first embodiment, and then radiated in the form of a radio wave through the radio antenna 21. Consequently, the encapsulated medical device 160 enables diagnosis of whether an abnormality is present in a direction of the depth of a deep region in a body cavity such as the small intestine 55. If the encapsulated medical device 160 is designed to have both the observation unit 24 and the ultrasonic unit 164, both the internal surface of a body cavity and a deep region in the body cavity can be assessed simultaneously.

Fourth Embodiment

FIG. 22A to FIG. 24B are concerned with a fourth embodiment of the present invention. FIG. 22A is a sectional view showing the structure of an encapsulated medical device in accordance with the fourth embodiment of the present invention. FIG. 22B is an F—F sectional view of the encapsulated medical device shown in FIG. 22A. FIG. 23A shows the appearance of the encapsulated medical device shown in FIG. 22A and FIG. 22B with a balloon thereof expanded. FIG. 23B is a G—G sectional view of the encapsulated medical device shown in FIG. 23A. FIG. 24A is a sectional view of an encapsulated medical device of a variant that has an armor member with a balloon freely detachably attached to the periphery of a capsule body. FIG. 24B is an H—H sectional view of the encapsulated medical device shown in FIG. 24A.

In the fourth embodiment, a capsule body has a balloon as an armor member. The other components are nearly identical to those of the third embodiment. The description of the identical components will be omitted, and the same reference numerals will be assigned to the identical components.

As shown in FIG. 22A and FIG. 22B, an encapsulated medical device 170 of the fourth embodiment has a capsule body 170A, which is nearly identical to the one included in the third embodiment, mounted in the front part of a flexible tube 172 that has a balloon 171 serving as an armor member. At this time, the capsule body 170A can be freely dismounted from the flexible tube 172.

The flexible tube 172 includes a balloon tube 173 that supplies or discharges a gas or a liquid 171a for expansion to or from the balloon 171, and an aeration/suction tube 174 for aerating the lumen of a body cavity or sucking air therefrom. The capsule body 170A is mounted in the flexible tube 172 composed of the balloon tube 173 and aeration/suction tube 174 with the front part thereof exposed in such a manner that a field of view offered by the observation unit 24 will not be obstructed by the flexible tube 172. The flexible tube 172 has the balloon tube 173 and aeration/suction tube 174 thereof bundled with a bundling member 175 such as a bundling band or tape.

The encapsulated medical device 170 has a gap 176, through which a fluid such as a gas or humor flows, formed as a fluid passage between the capsule body 170A and aeration/suction tube 174.

The encapsulated medical device 170 of the fourth embodiment having the foregoing components has the flexible tube 172, in which the capsule body 170A is mounted, inserted into a body cavity. As shown in FIG. 23A and FIG. 23B, the balloon 171 is expanded in an intended region in the lumen of a body cavity so that the front part of the encapsulated medical device 170 will be immobilized in the intended region in order to examine, cure, or treat the region.

At this time, the front part of the flexible tube 172 comes into close contact with the internal surface of the body cavity to block the lumen thereof. Owing to the gap 176 formed between the capsule body 170A and aeration/suction tube 174, a fluid such as a gas or humor can pass.

Consequently, the encapsulated medical device 170 of the fourth embodiment provides the same advantages as the first to third embodiments.

Moreover, as shown in FIG. 24A and FIG. 24B, an encapsulated medical device 180 has an armor member 182, which includes a balloon 181, freely detachably attached to the periphery of a capsule body 180A that is the same as the one included in the first embodiment. A patient swallows the encapsulated medical device 180.

In this case, when the balloon 181 is expanded, a fluid passage is formed between the capsule body 180A and the internal surface of the balloon 181 owing to the linkage hole or groove formed in the extended portion of the capsule body 180A. In FIG. 24B, the capsule body 180A has the linkage groove 73 formed in the extended portion 72 thereof.

The capsule body 180A has the observation unit 24 and illuminator 23 incorporated in the distal and back parts thereof. The balloon 181 has an infusion port 182b, through which an expansion gas or liquid 181a is infused thereinto, bored therein.

The balloon 181 has the expansion gas or liquid 181a infused through the infusion port 182b thereof using a treatment appliance such as an injection needle inserted into a treatment appliance passage channel running through an endoscope that is not shown.

Consequently, the encapsulated medical device 180 can be more compact than the encapsulated medical device 170 and constructed more easily.

According to the present invention, it is apparent that a wide range of different embodiment can be constructed based on the invention without a departure from the spirit and scope of the invention. The present invention will be limited to the appended claims but not restricted to any specific embodiment.

What is claimed is:

1. An encapsulated medical device comprising:
   a capsule body capable of passing through the lumen of a body cavity to permit examination or treatment; and
   fluid passage forming means, included in said capsule body, for when said capsule body passes through the lumen of a body cavity, if said capsule body comes into close contact with the internal surface of the body cavity to block the lumen thereof, forming a fluid passage that links the forward and backward parts of the lumen of the body cavity.

2. The encapsulated medical device according to claim 1, wherein said fluid passage forming means is formed directly in said capsule body or in an armor member that is freely detachably attached to the periphery of said capsule body.

3. The encapsulated medical device according to claim 1, wherein: said fluid passage forming means is realized with an extended portion of said capsule body, of which cross section cut at right angle to the longitudinal axis thereof is non-circular, formed at an end of one axis of the cross section of said capsule body;
   provided that said capsule body does not have the extended portion, the cross section of said capsule body is substantially circular; and
   said fluid passage forming means forms a fluid passage.

4. The encapsulated medical device according to claim 1, wherein a plurality of fluid passages are formed in one direction with respect to the longitudinal axis of said capsule body.

5. The encapsulated medical device according to claim 1, wherein said capsule body includes at least observing means.

6. The encapsulated medical device according to claim 1, wherein a plurality of fluid passages are formed substantially symmetrically to one another with respect to the longitudinal axis of said capsule body.

7. The encapsulated medical device according to claim 1, wherein said capsule body has a plurality of hard members linked by a flexible string-like member.

8. The encapsulated medical device according to claim 1, wherein said capsule body has a switch, which is used to control a battery that supplies power and to control power supply from the battery, incorporated therein.

9. The encapsulated medical device according to claim 1, wherein said capsule body includes at least one medical-purpose examining means such as arm optical sensor, a pH sensor, a temperature sensor, a pressure sensor, or an ultrasonic probe.

10. The encapsulated medical device according to claim 1, wherein said capsule body includes at least one opening means for a treating or examining means, such as, a medicine administration port or a humor infusion port.

11. The encapsulated medical device according to claim 1, wherein said capsule body includes at least one treating means such as an injection needle.

12. The encapsulated medical device according to claim 1, wherein said fluid passage is realized with a spiral groove.

13. The encapsulated medical device according to claim 1, wherein said capsule body has at least a magnet incorporated therein.

14. The encapsulated medical device according to claim 1, wherein said capsule body has at least observing means and a magnet incorporated therein, and said fluid passage is realized with a spiral groove.

15. The encapsulated medical device according to claim 2, wherein said fluid passage is realized with a linkage hole formed between said capsule body and said armor member or in said armor member.

16. The encapsulated medical device according to claim 2, wherein said fluid passage is realized with a linkage groove formed in said armor member.

17. The encapsulated medical device according to claim 2, wherein a plurality of projections are formed on said armor member, and said fluid passage is realized with a plurality of concave parts formed among said plurality of projections.

18. The encapsulated medical device according to claim 2, wherein said armor member is realized with a hard tubular member, and said fluid passage is formed with the internal surface of said tubular member and notches formed in the periphery of said capsule body.

19. The encapsulated medical device according to claim 2, wherein said armor member is a transparent member formed to enclose the entire periphery of said capsule body, and said fluid passage is formed in said transparent member or between the internal surface of said transparent member and the periphery of said capsule body.

20. The encapsulated medical device according to claim 2, wherein said armor member is a mesh cover attached to the periphery of said capsule body, and the small holes of the mesh of the mesh cover realize said fluid passage.

21. The encapsulated medical device according to claim 2, wherein said armor member is a sack-like elastic balloon capable of expanding outwards beyond the periphery of said capsule body, and said fluid passage is formed between the internal surface of the elastic balloon and the periphery of said capsule body.

22. The encapsulated medical device according to claim 2, wherein said fluid passage is realized with a linkage hole or linkage groove formed in said capsule body.

23. The encapsulated medical device according to claim 2, wherein a plurality of projections are formed on said capsule body, and said fluid passage is realized with a plurality of concave parts formed among said plurality of projections.

24. The encapsulated medical device according to claim 2, wherein said fluid passage is realized with a spiral groove formed in said armor member.

25. The encapsulated medical device according to claim 2, wherein said armor member is an elastic member.

26. The encapsulated medical device according to claim 5, wherein:

said capsule body has the center axis thereof, which passes the center of the minor axis of a cross section thereof cut at right angle to the longitudinal axis thereof, deviated from the optical axis of said observing means; and said fluid passage is formed in a space extending on the opposite side of the center axis, which passes the center of the minor axis of the cross section cut at right angle to the longitudinal axis, relative to the optical axis of said observing means.

27. The encapsulated medical device according to claim 5, wherein said capsule body includes a plurality of observing means that permits observation in different directions.

28. The encapsulated medical device according to claim 20, wherein said mesh cover does not cover at least a portion falling within a range of observation offered by said observing means.

29. A method of examining or treating an internal region of a body cavity using an encapsulated medical device that includes a capsule body and fluid passage forming means for forming a fluid passage that links the forward and backward parts of the lumen of the body cavity when said capsule body comes into close contact with the internal surface of the body cavity to block the lumen thereof.

30. A method of examining or treating an internal region of a body cavity using an encapsulated medical device, wherein said encapsulated medical device includes a capsule body and fluid passage forming means that forms a fluid passage which links the forward and backward parts of the lumen of the body cavity when said capsule body comes into close contact with the internal surface of the body cavity to block the lumen thereof.

31. The method according to claim 30, wherein the lumen of a body cavity is the lumen of the small or large intestine.

* * * * *